(12) United States Patent
Chen et al.

(10) Patent No.: US 10,793,881 B2
(45) Date of Patent: Oct. 6, 2020

(54) METHOD FOR THE MICROBIAL PRODUCTION OF 8-METHYL NONANOIC ACID

(71) Applicant: Conagen Inc., Bedford, MA (US)

(72) Inventors: Hui Chen, North Billerica, MA (US); Xiaodan Yu, Lexington, MA (US)

(73) Assignee: Conagen Inc., Bedford, MA (US)

( * ) Notice: Subject to any disclaimer, the term of this patent is extended or adjusted under 35 U.S.C. 154(b) by 0 days.

(21) Appl. No.: 16/444,305

(22) Filed: Jun. 18, 2019

(65) Prior Publication Data

US 2019/0390231 A1 Dec. 26, 2019

Related U.S. Application Data

(63) Continuation of application No. PCT/US2017/068085, filed on Dec. 22, 2017.

(60) Provisional application No. 62/437,792, filed on Dec. 22, 2016.

(51) Int. Cl.
- *C12P 7/40* (2006.01)
- *C12P 7/64* (2006.01)
- *C12N 9/10* (2006.01)

(52) U.S. Cl.
CPC .................. *C12P 7/40* (2013.01); *C12N 9/13* (2013.01); *C12P 7/6409* (2013.01); *C12Y 208/03001* (2013.01); *C12Y 208/03008* (2013.01); *C12Y 301/02014* (2013.01)

(58) Field of Classification Search
None
See application file for complete search history.

(56) References Cited

U.S. PATENT DOCUMENTS

| 9,371,549 B2 | 6/2016 | Silverman et al. |
| 2003/0145350 A1 | 7/2003 | Spener et al. |
| 2013/0005003 A1 | 1/2013 | Roessler et al. |
| 2013/0029387 A1 | 1/2013 | Nikolau et al. |
| 2016/0138061 A1 | 5/2016 | Haas et al. |
| 2016/0168603 A1 | 6/2016 | Garg et al. |

OTHER PUBLICATIONS

Extended Eurpoean Search Report for EP 17882749.9, dated Aug. 7, 2020.*
International Search Report and Written Opinion for PCT/US2017/068085, dated May 4, 2018.
International Preliminary Report on Patentability for PCT/US2017/068085, dated Jul. 24, 2019.
[No Author Listed], Invitrogen S.O.C. Medium Catalog No. 15544-034. 2002. 1 page.
Ashrafi et al., De novo assembly of the pepper transcriptome (*Capsicum annuum*): a benchmark for in silico discovery of SNPs, SSRs and candidate genes. BMC Genomics. Oct. 30, 2012;13(571):1-15.
GenBank Accession No. JW054178.1. Sep. 1, 2012. 1 page.
Kozik et al., CLPY5434.bl_C15.abl CLP(XYZ) lettuce perennis *Lactuca perennis* cDNA 25 clone CLPY5434, mRNA sequence. Genbank entry [online]. National Center for Biotechnolgy Information. Oct. 6, 2006, [Retrieved on Mar. 23, 2018]. Retrieved from the Internet: <URL:https://www.ncbi.nlm.nih.gov/nucest/DW094259.1 ?report=genbank>; 2 pages.
Mazourek et al., A dynamic interface for capsaicinoid systems biology. Plant Physiol. Aug. 2009;150(4):1806-21. doi: 10.1104/pp.109.136549. Epub Jun. 24, 2009.
NCBI Reference Sequence: XP 016564091.1. May 5, 2016. 1 page.
Qin et al., Whole-genome sequencing of cultivated and wild peppers provides insights into Capsicum domestication and specialization. Proc Natl Acad Sci U S A. Apr. 8, 2014;111(14):5135-40. doi: 10.1073/pnas.1400975111. Epub Mar. 3, 2014.
Simbaqueba et al., Development and characterization of microsatellite markers for the Cape gooseberry *Physalis peruviana*. PLoS One. 2011;6(10):e26719. doi: 10.1371/journal.pone.0026719. Epub Oct. 21, 2011.
Zhang et al., Efficient free fatty acid production in *Escherichia coli* using plant acyl-ACP thioesterases. Metabolic Engineering. 2011; 13:713-722.

\* cited by examiner

*Primary Examiner* — Suzanne M Noakes
(74) *Attorney, Agent, or Firm* — Wolf, Greenfield & Sacks, P.C.; Karen K. Chan

(57) ABSTRACT

The present disclosure relates to the production of 8-methyl nonanoic acid and medium chain branched fatty acids, e.g., via microbial fermentation.

16 Claims, 9 Drawing Sheets

Specification includes a Sequence Listing.

SEQUENCE LISTING

```
<160> NUMBER OF SEQ ID NOS: 9

<210> SEQ ID NO 1
<211> LENGTH: 1119
<212> TYPE: DNA
<213> ORGANISM: Capsicum annuum

<400> SEQUENCE: 1
atgtcgttga tgatcaggga tttgagcagt ttacattaca cagataattt ctggaaaaca      60
gagaagcatg tgatggaatg ccggagtttg aaatttgatt gtaacgcgaa gaagaaatgg     120
agagcgataa ctgctagtgc agacagtagc ggaagcagaa gcattgatac aattaatggg     180
aagaagataa atggtgttca tgttgagggg cactcgcaat caggacaaag gggaaatgta     240
gttgaatcag gatcatcatc atcaccgaaa cattcatata tgttagggaa ttttgtggag     300
gataaggttg tgtataggca gtcatttgtg attaggtctt atgaaattgg acctgataaa     360
actgctacta tggaaactat catgaatctc cttcaggaga cagctctaaa tcatgtggcg     420
aactcagggg ttggtagtag tggattcggg gctacacgag agatgagcct taggaaactc     480
atatgggtag tcactcgcat acatatacaa attgaacaat atagctcttg gggagatgtg     540
```

-continued

```
gtagagatcg atacatgggt agatgcagca ggcaaaaatg gaatgagaag ggattggatc    600
attcgcgact ccaacactcg caaaatcatc actagagcaa caagtaaatg ggtgataatg    660
aacatagaaa caagaaggtt atccaaaatc ccagagcagg tcaaagcaga agttcgacct    720
ttctacatca acagattcgc gatccctact gcacaaattg actctgaaaa gattgagaaa    780
ctcaacgatg aaactgccca aatcatctct tccggcttag ctccgcgatg gagcgacatg    840
gatgctaatc aacatgtcaa caatgtcaaa tatattggat ggattttgga gagtgtgccc    900
ataaatgttt tagaagacta ctacttaatg agcttgacat tagagtatag acgtgaatgt    960
caattatcaa atgtgctgca atccatgaca actatgcgag aaatagcaac atcagcaagt   1020
gataaaaatt gtggacttga atgcacacat ctgattcgaa tggaggctga tcgagctgag   1080
gttgttcgag caaggtccct atggcagcca aaacagtga                          1119
```

<210> SEQ ID NO 2
<211> LENGTH: 372
<212> TYPE: PRT
<213> ORGANISM: Capsicum annuum

<400> SEQUENCE: 2

```
Met Ser Leu Met Ile Arg Asp Leu Ser Ser Leu His Tyr Thr Asp Asn
1               5                   10                  15

Phe Trp Lys Thr Glu Lys His Val Met Glu Cys Arg Ser Leu Lys Phe
            20                  25                  30

Asp Cys Asn Ala Lys Lys Lys Trp Arg Ala Ile Thr Ala Ser Ala Asp
        35                  40                  45

Ser Ser Gly Ser Arg Ser Ile Asp Thr Ile Asn Gly Lys Lys Ile Asn
    50                  55                  60

Gly Val His Val Glu Gly His Ser Gln Ser Gly Gln Arg Gly Asn Val
65                  70                  75                  80

Val Glu Ser Gly Ser Ser Ser Pro Lys His Ser Tyr Met Leu Gly
                85                  90                  95

Asn Phe Val Glu Asp Lys Val Val Tyr Arg Gln Ser Phe Val Ile Arg
            100                 105                 110

Ser Tyr Glu Ile Gly Pro Asp Lys Thr Ala Thr Met Glu Thr Ile Met
        115                 120                 125

Asn Leu Leu Gln Glu Thr Ala Leu Asn His Val Ala Asn Ser Gly Val
    130                 135                 140

Gly Ser Ser Gly Phe Gly Ala Thr Arg Glu Met Ser Leu Arg Lys Leu
145                 150                 155                 160

Ile Trp Val Val Thr Arg Ile His Ile Gln Ile Glu Gln Tyr Ser Ser
                165                 170                 175

Trp Gly Asp Val Val Glu Ile Asp Thr Trp Val Asp Ala Ala Gly Lys
            180                 185                 190

Asn Gly Met Arg Arg Asp Trp Ile Ile Arg Asp Ser Asn Thr Arg Lys
        195                 200                 205

Ile Ile Thr Arg Ala Thr Ser Lys Trp Val Ile Met Asn Ile Glu Thr
    210                 215                 220

Arg Arg Leu Ser Lys Ile Pro Glu Gln Val Lys Ala Glu Val Arg Pro
225                 230                 235                 240

Phe Tyr Ile Asn Arg Phe Ala Ile Pro Thr Ala Gln Ile Asp Ser Glu
                245                 250                 255

Lys Ile Glu Lys Leu Asn Asp Thr Ala Gln Ile Ile Ser Ser Gly
            260                 265                 270
```

```
Leu Ala Pro Arg Trp Ser Asp Met Asp Ala Asn Gln His Val Asn Asn
            275                 280                 285

Val Lys Tyr Ile Gly Trp Ile Leu Glu Ser Val Pro Ile Asn Val Leu
        290                 295                 300

Glu Asp Tyr Tyr Leu Met Ser Leu Thr Leu Glu Tyr Arg Arg Glu Cys
305                 310                 315                 320

Gln Leu Ser Asn Val Leu Gln Ser Met Thr Thr Met Arg Glu Ile Ala
                325                 330                 335

Thr Ser Ala Ser Asp Lys Asn Cys Gly Leu Glu Cys Thr His Leu Ile
                340                 345                 350

Arg Met Glu Ala Asp Arg Ala Glu Val Val Arg Ala Arg Ser Leu Trp
            355                 360                 365

Gln Pro Lys Gln
    370

<210> SEQ ID NO 3
<211> LENGTH: 951
<212> TYPE: DNA
<213> ORGANISM: Artificial sequence
<220> FEATURE:
<223> OTHER INFORMATION: FatA

<400> SEQUENCE: 3
gcgaccaacg aaagagaatc taaaagtaaa cagcaggtca gtcacgaacc atcacttgct      60
gatcgtttac gtctggggac catgagtgaa gatggtatgt catataaaga gaaattcatc     120
gttcgctgct atgaagttgg cgttaataaa acgctgacgg ttgaaacaat tgctaatctg     180
ctgcaggaag taggttgtaa ccatgcacag agcgtgggct tcagcacaga tggctttgcg     240
actacccata gcatgcgtaa attacattta atttgggtta ctgcgcgtat gtatatcgaa     300
atttataaat atccggcttg gtctgatgtc gttgagattg agacatggtg ccagagtgaa     360
ggacgcatcg gtactcgccg cgattggatc ctgaaagatt gtgccacggg ggaggtcatc     420
ggacgcgcca cctcaaaatg gctgatgatg aatcaggata cacgtcgtct gcagaaagtt     480
acggatgagg taagagatga gttagagctg tatttcccga agaacttcg cctggctttt     540 cctgaagaaa acaatggctc actgaaaaaa attcctaaat tagaagatcc ggctgaatat     600
agtaaacttg gcctggtgcc tagacgtgca gatctggata tgaatcagca tgtgaacaat     660
gttacatata ttggttgggt cttggaaagt atgccgcagg agatcatcga tacgcatgag     720
ttagggacca ttacgattga ttatagaaga gagtgccagc acgatgatgt tgtggattct     780
ttaacctcag tggaaccgat cgaggatact gatgctttgg gtgcaaatgg gagcgcgaca     840
gcagcaaaag atgttaataa atcagtgctg catttctgc gtcttagtag tgatggcctg     900
gagatcaata atgtcgcac agagtggcgt aaaaaaccaa gccggattta a              951

<210> SEQ ID NO 4
<211> LENGTH: 1107
<212> TYPE: DNA
<213> ORGANISM: Artificial sequence
<220> FEATURE:
<223> OTHER INFORMATION: FatB

<400> SEQUENCE: 4
gcgaaagcca acgcacaggc tccgccgaaa gtgaatggca ccaaagtcgg tgtgatggat      60
ggctttaaaa cggatgacga agttattagc tctcatcacc cgcgtacctt catcaaccag     120
ctgccggatt ggagcatgct gctggcggcc attaccacga tctttctggc agctgaaaaa     180
```

```
caatggatga tgctggattg gaaaccgaaa cgtccggaca tgctggtcga tccgtttggc    240
ctgggtaaaa ttgtggaaga tggtttatc ttccgtcaga acttctcaat tcgctcgtat    300
gaaatcggcg cagatcgcac cgctagtatt gaaacgatga tgaaccatct gcaagaaacc    360
gcgctgaatc acgtgaaatc cgccggtctg atgcatggcg tttcggcag taccccggaa    420 atgtccaaac gtaatctgat ctgggtggtt acgaaaatgc aggtcgtgct ggatcgctac    480
ccgacctggg gtgacgttgt ccaagtggat acgtgggttg cggccagcgg caaaaacggt    540
atgcgtcgcg actggctgat tcgtgattct accacgggcg acgttctgat gcgcgcaagt    600
tcccagtggg tcatgatgaa taaagaaacc cgtcgcctga gcaaaattcc ggatgaagcg    660
cgtgccgaaa tcgaaggtta ttttgtcgac tcaccgccgg tgatcgatga cgattcgcgc    720
aaactgccga aactggatga aaccacggca gactataccc gcaccggtct gaccccgcgc    780
tggtcagacc tggatgtgaa ccagcacgtt aacaatgtca aatacattgg ttggattctg    840
gaatcggctc cgatgcaaat tctgaaggc tgcgaactgg cagctatgac gctggaatac    900
cgtcgcgaat gtcgtcgcga tagcgttctg cagagcctga cctctgttct ggataaagaa    960
gtcggcggtg acctgacgaa ctttggtcat gtggaatgcc aacacgttct gcgcctggaa    1020
aatggcggta agtggttaa aggccgtacc gaatggcgcc gaaactgat taatggcatc    1080 ggttctctgg gcggtttccc ggcctaa                                       1107

<210> SEQ ID NO 5
<211> LENGTH: 927
<212> TYPE: DNA
<213> ORGANISM: Artificial sequence
<220> FEATURE:
<223> OTHER INFORMATION: FatB2

<400> SEQUENCE: 5
ggtgtccatg tggaaggcca cagtcagtcc ggccaacgcg gtaacgtggt tgaatcaggt     60
agttcctcat cgccgaaaca ttcgtatatg ctgggcaatt ttgtggaaga taaagtcgtg    120
tatcgccaga gcttcgttat ccgttcttac gaaattggtc cggacaaaac cgcgacgatg    180
gaaaccatta tgaacctgct gcaagaaacg gcgctgaacc atgttgccaa tagcggcgtc    240
ggtagctctg gcttcggtgc gacccgtgaa atgtcactgc gcaaactgat ctgggttgtc    300
acgcgtattc acatccagat tgaacaatat agttcctggg gcgatgtggt tgaaattgat    360
acctgggtgg acgcggccgg caaaaacggt atgcgtcgcg attggattat ccgtgacagc    420
aatacccgca aaattatcac ccgtgctacg tctaaatggg ttatcatgaa tattgaaacc    480
cgtcgcctga gcaaaatccc ggaacaggtg aaagccgaag ttcgcccgtt ttacatcaac    540
cgtttcgcaa ttccgaccgc tcagatcgat agtgaaaaaa tcgaaaaact gaacgacgaa    600
acggcgcaaa ttatctcatc gggtctggcg ccgcgttggt ctgatatgga cgcaaaccag    660
catgttaaca acgtcaaata catcggctgg attctggaaa gtgtcccgat taatgtgctg    720
gaagattatt acctgatgtc cctgacccctg gaataccgtc gcgaatgtca gctgagtaac    780
gtgctgcaat ccatgaccac gatgcgcgaa atcgcgacct cagcctcgga taaaaattgc    840
ggcctggaat gtacgcacct gattcgtatg gaagcggacc gtgcggaagt ggtgcgtgct    900
cgttctctgt ggcagccgaa acaatga                                       927

<210> SEQ ID NO 6
<211> LENGTH: 1077
<212> TYPE: DNA
<213> ORGANISM: Artificial sequence
```

<220> FEATURE:
<223> OTHER INFORMATION: Kas IIIa optimized

<400> SEQUENCE: 6

| | | | | | |
|---|---|---|---|---|---|
| agtagtaccg | ttgagggtgc | ggataaattg | agcacggatc | agtcacgcgt | aagtcgtttg | 60 |
| gttagtcgcg | gatgtaaact | gattggctgt | ggcagtgcgg | tgccggcatt | gaaaatctcc | 120 |
| aacgatgatc | tggctaaaat | tgtagatact | aatgatgaat | ggatcagcgt | tcgtaccggg | 180 |
| atccgtaacc | gccgcgtgct | gtcaggtaaa | gataatctga | cggatttagc | tgcggaagcc | 240 |
| gcacgcaaag | cactggaaat | ggccgaggtc | gatcctaacg | atattgattt | gattctgctt | 300 |
| tgttcatcca | cccctgagga | tctgtttggc | agcgcacctc | agattcagaa | agctttgggt | 360 |
| tgcaaaagta | atccactggc | gtttgatatt | acagccgcgt | gtagcggatt | tatgctgggt | 420 |
| ttggtaagcg | ccgcctgtta | tattcgcgga | ggagggttca | aaaacgtatt | agtggttggc | 480 |
| gcagatgcgc | tgtcacggta | tgtagattgg | accgatcgcg | ggacgtgtat | tcttttttggt | 540 |
| gatgcggcag | gggcggttgt | tatgcaggcc | tgtgatattg | gagaggatgg | tcttttcggg | 600 |
| tttgatctgc | attctgatgg | cgagggtcag | cgccatctga | acgcctcctt | taaagagaac | 660 |
| gagtcagatc | gggcctgcgg | taccaacggt | agtgttattg | gattccctcc | gaaaacgagc | 720 |
| tcatattcct | gtattcagat | gaacggtaaa | gaagtgttca | gatttgctgt | gcgggtggtg | 780 |
| cctcagagca | tcgaggcagc | actggagaat | gctggcctgc | ctcagtctaa | aattgattgg | 840 |
| cttctgttac | accaggcgaa | tcagcgcatc | attgatgcag | tcgccacgcg | tctggaggtg | 900 |
| ccgtccgagc | atgtgatttc | taatttatca | aattatggaa | atacatcagc | agcgagtatt | 960 |
| cctctggctc | tggatgaagc | agttcgtagc | ggtaaagttc | aggctgggca | tgtcattgca | 1020 |
| gccgctggtt | ttggtgcagg | actgacctgg | ggaagcgcta | ttttgagatg | gggctaa | 1077 |

<210> SEQ ID NO 7
<211> LENGTH: 1050
<212> TYPE: DNA
<213> ORGANISM: Artificial sequence
<220> FEATURE:
<223> OTHER INFORMATION: KAS IIIb optimized

<400> SEQUENCE: 7

| | | | | | |
|---|---|---|---|---|---|
| gccaaaggcg | cagtggaact | gagccgtctg | gttaataccg | gttgcaaact | ggtgggctgt | 60 |
| ggttcagctg | tgccgtcgct | gcgcgttagc | aacaatgatc | tggcaaaaat | cgtcgatacc | 120 |
| aatgacgaat | ggatttctgt | gcgtacgggc | atccgccatc | gtcgcgttct | gagtggtaaa | 180 |
| gaaaacctga | cggatctggc | catcgaagcg | gcctggaaag | ctctggaaat | ggcggacgtc | 240 |
| ccgccggaag | atgtggacct | gattctgatg | tgcagctcta | ccggcgatga | cctgtttggt | 300 |
| tctgccccgg | tgatccagaa | agcactgggc | tgtaaacgta | tccgctggc | gttcgatatt | 360 |
| acggcagctt | gcagtggctt | tctgctgggt | ctgttctcag | cttcgtgtta | tattaaagcg | 420 |
| ggcggtttta | aaaacgtcct | ggtgattggc | gccgatgcag | tttcccgttt | tatcgattgg | 480 |
| accgaccgcg | gttcatgcat | tctgttcggc | gatgcggccg | gtgctgttct | ggtccaggcg | 540 |
| tgtgatatcg | gtgaagacgg | cctgtttggt | ttcgatctgc | attcggatgg | cgacggtaaa | 600 |
| cgccacctga | ttagcacctt | taaagaaaat | gaaacggatg | acgcctcgaa | cgaaaatcac | 660 |
| agcgtcacct | cttttcccgcc | gaaatgcagt | tcctattcat | acctgcagat | gaacggcaaa | 720 |
| gaaatctta | aattcgcggt | tcgtgtggtt | ccgcaatcca | ttgaagcagc | tctgaaaaaa | 780 |
| gccggcctgg | atggttcaaa | caattttgac | tggctgctgc | tgcatcaggc | caaccaacgc | 840 |

| | |
|---|---|
| attatcgatg gcatcgcaac ccgtctggaa gttccgtctg aacgcgtcat tagtaacctg | 900 |
| gcaaattacg gtaacacgag tgccgcatcc attccgctgg cactggatga agcagtgcag | 960 |
| gacggcaaag ttcaaccggg tcacgtcatt gcagcggccg ttttggtgc cggtctgacc | 1020 |
| tgggctagcg cgattttccg ttggggttaa | 1050 |

<210> SEQ ID NO 8
<211> LENGTH: 1671
<212> TYPE: DNA
<213> ORGANISM: Artificial sequence
<220> FEATURE:
<223> OTHER INFORMATION: CCL4 optimized

<400> SEQUENCE: 8

| | |
|---|---|
| atggaagacc tgaaaccgcg tccggcatcg tcctccccgc tgacccccgct gggctttctg | 60 |
| gaacgtgctg cgaccgtgta tggtgactgc acctctgtgg tttatgatgc ggttagctac | 120 |
| acctggtctc agacgcatcg tcgctgcctg tgtctggcga gctctattgc ctcactgggc | 180 |
| atcgaaaacg gtcatgtcgt gtcggtcctg gccccgaatg tgccgcaaat gtatgaactg | 240 |
| cactttgcag tcccgatggc aggtgctatt ctgaacgcag tgaatctgcg tctggatgct | 300 |
| cgcaccattt caatcctgct gcatcacagt gaatccaaac tgatcttcgt ggatcacctg | 360 |
| tcgcgtgacc tgattctgga agcgatcgcc ctgtttccga acaggcaccg gtgccgcgc | 420 |
| ctggttttca tggctgatga atcagaatcg gcaacagtt ccgaactggg taagaatttt | 480 |
| ttctgctctt acaaagatct gattgaccgt ggtgatccgg actttaaatg ggtgatgccg | 540 |
| aaaagcgaat gggacccgat gatcctgaat tacacctctg caccacgtc atcgccgaaa | 600 |
| ggtgttgtcc attgtcaccg cggcattttc atcatgaccg ttgatagtct gattgactgg | 660 |
| ggcgttccga acagccggt ctatctgtgg acgctgccga tgtttcatgc gaatggttgg | 720 |
| agctatccgt ggggtatggc cgcggtgggc ggtaccaata tttgcctgcg taaattcgat | 780 |
| tctgaaatca tctacgacat gatcaaacgc atggcgtta cgcacatgtg tggtgcgccg | 840 |
| gtggttctga acatgctgtc aaatgccccg ggttcggaac cgctgaaaac cacggtgcaa | 900 |
| attatgaccg caggtgcacc gccgccgagc gcagttctgt ttcgtacgga aagcctgggt | 960 |
| ttcgctgtct ctcatggcta cggtctgacc gaaacggcgg gcctggtcgt gagttgtgcc | 1020 |
| tggaagaaag aatggaacca cctgccggca accgaacgtg ctcgcctgaa atcccgccag | 1080 |
| ggcgttggta ccgtcatgca acgaaaatt gatgttgtcg acccggtgac cggtgcagct | 1140 |
| gttaaacgtg acggcagtac gctgggtaa gtggttctgc gcggcggttc cgtgatgctg | 1200 |
| ggttatctga agatccgga aggcaccgcg aaatccatga cggccgatgg ttggttttat | 1260 |
| accggcgacg tgggtgttat gcatccggat ggctacctgg aaatcaaaga tcgtagtaaa | 1320 |
| gacgttatca tctccggcgg tgaaaatctg agctctgtcg aagtggaaag tattctgtac | 1380 |
| tcccatccgg acattctgga agccgcggtt gtggcccgtc cggatgaatt tgggggtgaa | 1440 |
| accccgtgcg ccttcgtgtc actgaagaaa ggcctgacca aaaaaccgac ggaaaaagaa | 1500 |
| attgtggaat attgtcgttc gaaactgccg cgctacatgg ttccgaaaac cgttgtcttt | 1560 |
| aaagaagaac tgccgaaaac cagcacgggc aaagtgcaga aattcatcct gcgtgatatg | 1620 |
| gctcgtggta tgggctcggc gaccgcaggt gcttcccgct cccgtatgta a | 1671 |

<210> SEQ ID NO 9
<211> LENGTH: 1554
<212> TYPE: DNA
<213> ORGANISM: Artificial sequence

```
<220> FEATURE:
<223> OTHER INFORMATION: PCT optimized

<400> SEQUENCE: 9
atgcgtaaag tggaaattat caccgcggaa caggcggccc aactggttaa agataacgac      60
accattacga gcatcggttt tgtcagctct gcacatccgg aagctctgac gaaagcgctg     120
gaaaaacgtt tcctggatac caacacgccg cagaatctga cctatattta cgccggttct     180
caaggcaaac gtgatggccg cgcagctgaa catctggctc acacgggtct gctgaaacgc     240
gcgattatcg gccactggca gaccgtgccg gctattggta aactggcggt tgaaaacaaa     300
atcgaagcat acaacttcag tcagggcacc ctggttcatt ggttccgtgc actggctggt     360
cacaaactgg gcgtgtttac ggatattggt ctggaaacct tcctggaccc gcgccagctg     420
ggcggtaaac tgaacgatgt tacgaaagaa gacctggtta aactgatcga agtcgatggc     480
catgaacagc tgttttatcc gaccttcccg gttaacgtcg cttttctgcg cggcacgtac     540
gcggatgaaa gtggcaatat taccatggac gaagaaatcg gtccgttcga atcaacctcg     600
gtcgcgcagg ccgtgcataa ttgcggcggt aaagtggttg tccaagtgaa agatgtggtt     660
gcccacggtt ccctggaccc gcgtatggtc aaaattccgg gcatctatgt ggattacgtc     720
gtggttgcgg ccccggaaga ccatcagcaa acgtatgatt gtgaatacga tccgagcctg     780
agcggtgaac atcgtgcacc ggaaggtgca accgatgcag ctctgccgat gtcagcgaag     840
aaaattattg gtcgtcgcgg cgccctggaa ctgaccgaaa acgcagtcgt gaatctgggt     900
gtgggcgcac cggaatatgt ggcgtcggtt gccggtgaag aaggcattgc ggataccatc     960
acgctgaccg tcgaaggcgg tgccattggc ggtgtgccgc agggcggtgc acgttttggt    1020
agttcccgca acgcagatgc tattatcgac cataccctatc agtttgattt ctacgacggc    1080
ggtggcctgg atattgccta tctgggcctg gcacaatgcg acggtagtgg caacatcaat    1140
gtttccaaat ttggtacgaa tgtcgccggc tgcggtggct tcccgaacat ttctcagcaa    1200
accccgaatg tttacttttg tggcacgttc accgcgggcg gcctgaaaat tgcggtggaa    1260
gatggtaaag ttaaaatcct gcaggaaggc aaagccaaaa aattcatcaa agcagtggat    1320
caaatcacct tcaacggtag ctatgcgccc cgtaatggca acatgttct gtacattacg     1380 gaacgctgtg tctttgaact gaccaaagaa ggtctgaaac tgattgaagt ggctccgggc    1440
attgatatcg aaaaagacat cctggcccac atggatttta aaccgattat cgacaatccg    1500
aaactgatgg atgcgcgtct gttccaggac ggtccgatgg gcctgaaaaa ataa          1554
```

METHOD FOR THE MICROBIAL PRODUCTION OF 8-METHYL NONANOIC ACID

CROSS-REFERENCE TO RELATED APPLICATIONS

This application is a continuation of International Patent Application Serial No. PCT/US2017/068085, filed Dec. 22, 2017, which claims priority to U.S. Provisional Application No. 62/437,792, filed on Dec. 22, 2016, the contents of each of which are incorporated by reference herein in their entirety.

FIELD OF THE INVENTION

The field of the invention relates to methods and processes useful in the microbial production of 8-methyl nonanoic acid (CAS No. 5963-14-4) (hereinafter "8M"), an immediate precursor to capsaicin. Importantly, the current disclosure provides a method to produce 8M in yields not possible in plant-based systems and the sequence for the FatB2 protein. The present disclosure provides a genetically modified E. coli strain that has been modified to biosynthesize 8M, a method of producing the genetically modified microorganism to produce 8M, and a production method to produce 8M in high yield and purity levels starting from a specific starting material. In this disclosure, the KASIIIa, KASIIIb, FatB, and FatB2 genes were identified and characterized, including their involvement in the biosynthesis of 8M.

BACKGROUND OF THE INVENTION

The present disclosure is directed, in some embodiments, to a method for modifying a microbial strain to produce 8-methyl nonanoic acid (also known as "isocapric acid"), a desirable branched medium chain fatty acid compound in high yield, using a glucose or isobutyric acid as a feeding source depending on different pathways exploited for isobutryl-CoA formation for the microbial production strain. Capsaicinoid compounds (including without limitation: capsaicin (CP), dihydrocapsaicin (DHCP), nonivamide (NV)), are the "spicy" components of hot peppers, and may be effective for preventing a number of pathologies by promoting energy metabolism, stimulating the central nervous system and helping in weight loss via activating lipolytic enzymes. In addition, these compounds can act to sterilize the Gastrointestinal tract, improve immunity when consumed and are also effective for activating immunity and relieving fatigue. In the production of capsaicin, the 8M compound is an essential intermediate and degradation product of CP (FIG. 1).
Capsaicinoid Chemistry "Spiciness" or pungency is a unique characteristic of hot peppers in the *Capsicum* genus that produce alkaloids called capsaicinoids. In nature, it is believed that capsaicinoids are present in plants to deter mammals from consuming their fruits and destroying seeds. Humans can sense capsaicinoids via a receptor structurally related to members of the transient receptor potential channels (or "TRP" family of ion channels). Similar to other receptors important in sensory neurons, the capsaicin receptor ("TRPV1" also referred to as the vanilloid TRP, vanilloid 1 Receptor or the TRPV1) mediates the pungent odor and pain/hot sensations associated with capsaicin and piperine by reversibly losing sensitivity to capsaicin as well as other pain and heat stimuli when it is under prolonged exposure to the same stimulus (Caterina et al., 1997). This phenomenon may partially explain why humans can tolerate and even enjoy spicy foods, as pain sensors may be turned off after extensive exposure.

Capsaicin (CP), 8-methyl-N-vanillyl-trans-6-nonenamide, and dihydrocapsaicin (DHCP), 8-methyl-N-vanillyl-nonanamide, are the two major capsaicinoids typically found in plants together they are responsible for up to 90% of the pungency (Garcés-Claver et al., 2007) of the pepper family. Relative to the current disclosure 8M is an immediate biosynthetic precursor to CP but is generally only available in vanishingly small amounts when sourced from plant-based materials.

Speaking generally, the capsaicin content of chili peppers ranges from 0.1 to 1% w/w (Govindarajan and Sathyanarayana 1991) and for many uses requires that methods be used to concentrate the CP and/or DHCP compounds for any industrial or commercial use. As for 8M, it significantly increases the yield of capsaicin when added to immobilized and freely suspended cells of *C. frutescens* but is almost impossible to extract in appreciable amounts from plant-based sources.

In addition to their primary use in food as an ingredient or minor additive, capsaicinoids have many pharmaceutical and medical uses. They have been found to exert a series of physiological and pharmacological effects, including analgesia, anticancer, anti-inflammatory, anti-oxidative and anti-obesity activities and are used as the main components of ointments, patches, oils and creams designed to relieve pain caused by several diseases such as vasomotor rhinitis, osteoarthritis and rheumatoid arthritis (Aza-Gonzalez et al., 2011). Capsaicinoids are currently used as the main active ingredient in self-protection aerosol sprays on the market (Reilly et al., 2001 popularly called "pepper spray"). In addition, recently capsaicinoid consumption was reported to lower plasma cholesterol and improve endothelial function in hamsters (Liang et al., 2013). Due to these diverse and growing uses of capsaicinoids including 8M in food, medicine and defense, the demand in the international market for the capsaicin and capsaicinoids is increasing.

The *Capsicum* genus includes over 20 species of peppers, from which *C. annuum*, *C. frutescens*, *C. chinense*, *C. baccatum*, and *C. pubescens* have been domesticated (Walsh and Hoot, 2001). There is wide genetic variation in pungency or spiciness levels across the various *Capsicum* species due to varying levels and types of capsaicinoids present. For example, the non-pungent sweet bell pepper from *C. annuum* scored 0.0 SHU (Scoville Heat Unit; a scale that indicates the amount of capsaicin), while the "Bhut Jolokia" or ghost chili is a hybrid between *C. chinense* and *C. frutescens* from Northeastern India, scored up to 1,001,304 SHUs (Bosland and Baral, 2007) (see Table 1).

TABLE 1

| Capsaicinoid Name | Abbrev. | Typical relative amount | Scoville heat units | Chemical structure |
|---|---|---|---|---|
| Capsaicin | C | 69% | 16,000,000 | 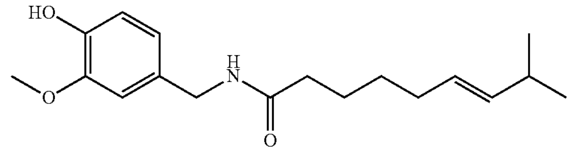 [SMILES: COc1cc(CNC(=O)CCCC/C=C/C(C)C)ccc1O] |
| Dihydrocapsaicin | DHCP | 22% | 15,000,000 | 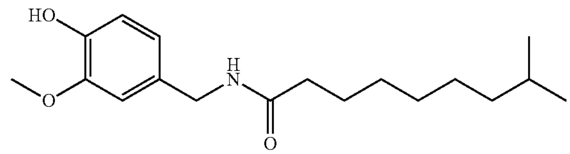 [SMILES: COc1cc(CNC(=O)CCCCCCC(C)C)ccc1O] |
| Nordihydrocapsaicin | NDHC | 7% | 9,100,000 | 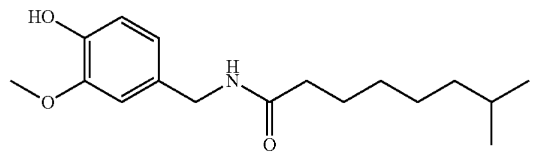 [SMILES: COc1cc(CNC(=O)CCCCCC(C)C)ccc1O] |
| Homodihydrocapsaicin | HDHC | 1% | 8,600,000 | 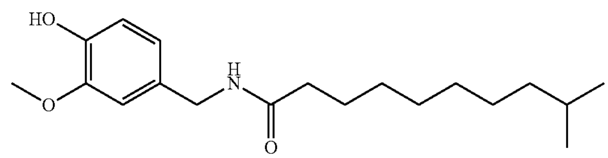 [SMILES: COc1cc(CNC(=O)CCCCCCCC(C)C)ccc1O] |
| Homocapsaicin | HC | 1% | 8,600,000 | 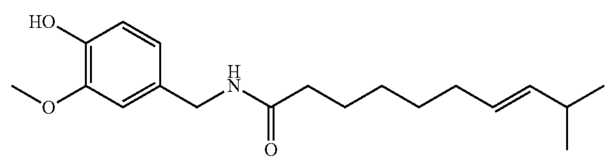 [SMILES: COc1cc(CNC(=O)CCCCC/C=C/C(C)C)ccc1O] |
| Nonivamide | NV | | 9,200,000 | 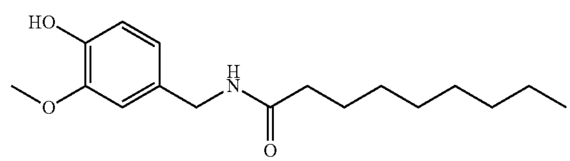 [SMILES: CCCCCCCCC(=O)NCc1ccc(O)c(OC)c1] |

In vivo, capsaicin is synthesized by capsaicin synthase (CS/AT3/Pun1), an acyltransferase that transfers the 8-methyl nonenoyl moiety from 8-methylnonenoyl-CoA to vanillylamine to form an amide conjugate (FIG. 1, Chen et al. 2015 and Ogawa et al. 2015). Vanillylamine is formed from the phenylpropanoid pathway whereas the branched-chain fatty acid is derived from a branched-chain amino acid, e.g. valine (Curry et al., 1999; Stewart et al. 2007; Mazourek et al., 2009). Limitations in the production and use of capsaicins primarily stems from the prior need to extract it from plants. Typically, pure CP extracted from plants typically rates at approximately 16,000,000 Scoville units on the heat index and in this concentration can sell for over $5000 USD per gram (Batchelor, 2000)(see Table 1). However, the content of capsaicinoids actually present in hot peppers is generally very low and can be greatly affected by environmental and growth conditions leading to problems of sustainability and consistency. The production of 8M can help solve this issue through its use as a capsaicin content enhancer when incubated with intact *C. frutescens* cells as well as its direct use in various pharmacological and commercial formulations. According to the current disclosure, in some embodiments, the identification of genes related to the biosynthesis of 8M will help to increase capsaicinoid production through bioconversion in modified microbes.

When extracted from plants, typically solid-liquid extraction using solvents like hexane, chloroform, and ethanol are commonly employed for capsaicinoid recovery (Catchpole et al., 2003). However, solvent extraction is itself energy intensive, leads to problems of toxic waste disposal, requires extensive acreage for the plants themselves to be grown and yields a product that requires further purification for minor constituents such as 8M to be recovered. Thus, new production methods are needed to reduce costs of pure capsaicin or 8M production and/or the recovery of other capsaicinoids and lessen the environmental impact of large scale cultivation and processing (Yao et al., 1994). Genetic manipulation of selected microbial strains has the potential to address these needed improvements and increase the selectivity, abundance and production of specific capsaicinoids.

It is estimated that about 60% of pure capsaicin currently produced is used as a raw material or ingredient in pharmaceuticals and about 15% is used in pesticides with the remainder being used as a food additive. As of 2016, capsaicin extract is priced at about $5,000 per kilogram in the current international market with 1,200 tons of global annual production.

In addition to the above, while consumers approve and actively seek natural and biological sources for food, fragrance, flavor or medicinal components they are also concerned about sourcing, consistent potency and environmentally sustainable production. Into this situation, the microbial fermentation and production methods of the current disclosure provide compounds produced by modified microbial strains that have the capability to produce products biologically in quantities useful for a variety of industries and research while doing so in a more natural fashion than organic chemical synthesis.

In the last three decades it has become evident that the world's fossil fuel reserves are decreasing and will eventually be depleted and will be unable to meet global need and/or will be cost prohibitive to recover. In response, the development of renewable resources has become a focus of governments and scientists alike. In this vein, the current disclosure provides for the production a medium chain (C8-C14) branched chain fatty acids which, if produced in volume, would provide a base for enhanced biofuels along with the other benefits provided herein. Therefore, a component of the current disclosure is in the focus on microbial fatty acid biosynthesis with the aim to produce medium-chain fatty acids or derivatives thereof for use in the production of diesel.

As an industrially important organism and with the best studied microbial fatty acid biosynthesis, E. coli has often been the organism of choice for studies into fatty acid biosynthesis. Plant-based production of fatty acids for fuel use is available but as world population grows a debate concerning the social and environmental consequences of the use of food and agricultural land for biofuel production has also grown. Relative to plant-based biofuel production the methods herein, in some embodiments, provide for the microbial production of medium chain (C8-C14) free fatty acids (FFA) useful in the production of biofuels. Such production would be beneficial for the quick production time and renewable nature. They also would avoid using agricultural land that could be otherwise occupied growing food for an increasing population.

Accordingly, a need exists for the development of a novel method of producing specific capsaicin intermediates, such as 8M, for consumers or for industrial needs. Specifically, the current disclosure provides, in some embodiments, methods to produce 8M from a fermentation process in commercially relevant amounts.

SUMMARY OF THE INVENTION

The present disclosure encompasses improved methods of producing 8-methyl nonanoic acid. The current disclosure provides, in some embodiments, a method to produce 8-methyl nonanoic acid in modified microbes that comprise a cellular system, such as yeast or bacteria. According to the current disclosure, a microbial fermentation process is provided that synthesizes 8M. In some embodiments, the cultures of the disclosure can produce 8M when the modified microbial strains are fed from natural precursors such as glucose or isobutyric acid. The identification of genes related to 8M production e. g. FatB and KASIII is also an essential part of this disclosure.

Due to the low-temperature operability of branched-chain fatty acids which are superior to straight chain fuels, several microbial fermentation processes to produce branched long-chain fatty acids have been described in the field of biofuel research (Howard et al. 2013; Haushalter et al. 2014; Jiang et al. 2015; Tao et al. 2015; and, Bentley et al. 2016). However, there has been no report on the ability to produce branched medium-chain fatty acid production using microbial fermentation techniques or methods, such as provided herein.

As shown in FIG. 1, an acyl-ACP thioesterase controls the chain length of fatty acid and is one of the key enzymes in 8M biosynthetic pathway. However, such an 8M-specific thioesterase has not been characterized thus far. Alum et al. (2003), using a differential expression technique isolated a FatA gene (GenBank: AF318288.1) from pepper fruits and it was theorized that this thioesterase could be involved in 8M biosynthesis (FIG. 1, Stewart et al. 2007). However, Aluru et al., did not provide the biochemical activity of FatA and no study since has reported on this feature of FatA. Using bioinformatics tools, Mazourek et al. (2009) isolated another acyl-ACP thioesterase, FatB (GenBank: EU616562) from hot peppers. Likewise, FatB has not been previously characterized thus far and its role in 8M biosynthesis is still unknown. In this application, we reported the identification of a third acyl-ACP thioesterase gene from the genome of *C. annuum* L_Zunla-1 (Qin et al. 2014) and named it FatB2 (NCBI Reference Sequence: XM_016708605.1). FatB2 has 372 aa which contains 64 aa of signal peptide that designate it as chloroplast targeted. (See SEQ IDS NOs 1 through 5).

In some embodiments, the current method provides an approach for the development of a bacterial strain that can produce significant volumes of 8-methyl nonanoic acid by genetic modification and targeted feeding of specific starting molecules that are more cost effective and easier to obtain. According to some embodiments of the current disclosure the production of isobutyryl-CoA is the key intermediate. Once it is produced, KASIIIa/KASIIIb are involved in its elongation, the thioesterase (FatB/FatB2) controls the length of elongated fatty acids. 8M is produced after 3 rounds of elongation with the cutting by FatB/FatB2. (See SEQ IDS NOs 6 through 9). Additional rounds can be included to further elongate the fatty acids produced hereby.

An embodiment of the present disclosure is a biosynthetic method of developing 8-methyl nonanoic acid by making isobutyryl-CoA from glucose or isobutyric acid.

In the current disclosure we demonstrated three ways of making isobutyryl-CoA: 1) de novo from glucose/pyruvate; 2) from ACS (AAE, acyl-CoA synthetase); and, 3) from PCT (propionate CoA-transferase). In some embodiments, this intermediate is itself key to producing 8M microbially.

In an alternative embodiment, the feeding of glucose to the cellular system comprises expressing the genes for de novo biosynthesis of isobutyryl-CoA in the cellular system. the feeding of isobutyric acid to the cellular system expressing a isobutyryl-CoA synthetase (ACS) gene or a propionate/isobutyrate-CoA transferase (PCT) gene.

The current disclosure provides, in part, three pathways for isobutyryl-CoA formation (see the publications cited below for additional pathway information) and thereafter the production of branched medium-chain fatty acids in engineered microbes:

1. For de novo using alsS, ilvC, ilvD and bkd genes (Jiang et al.,);
2. Using the ACS (AAE) pathway, (Zhang et al.,); and,
3. Using the PCT pathway, (McMahon M D et al.,)

In terms of product/commercial utility there are several dozen products containing capsaicin or close analogs such as 8M on the market in the United States and can be used in everything from analgesics to pest repellents as well as in foods and as an exercise supplement. Products containing 8M can be aerosols, liquids, or granular formulations.

According to some embodiments of the current disclosure, medium chain (C8 through C14) branched-chain fatty acids (BCFAs) can be produced for use in biofuel production. These molecules are important in the development of biofuels as they enhance the operating temperature range of the fuel, especially with regard to developing fuels that have superior cold-flow properties. Single chain fatty acids (SC-FAs) by contrast appear much easier to produce via microbial bioconversion. Cellular synthesis of both SCFAs and BCFAs requires the FabH enzyme that can catalyze condensation reactions between malonyl-ACP and a short-chain acyl-CoA.

In some aspects, the disclosure provides a biosynthetic method of making the capsaicinoid 8-methyl nonanoic acid (8M) comprising (a) expressing KASIIIa, KASIIIb and a thioesterase in a transformed cellular system; (b) producing isobutryl-CoA in the transformed cellular system; and, (c) producing 8-methyl nonanoic acid.

In some embodiments of the method, the thioesterase is FATB or FATB2. In some embodiments of the method, the KASIIIa is cloned from a plant of the *Capsicum* genus (e.g., ghost chili). In some embodiments of the method, the KASIIIb is cloned from a plant of the *Capsicum* genus (e.g., ghost chili). In some embodiments of the method, the thioesterase is FATB2 and it is cloned from a plant of the *Capsicum* genus (e.g., ghost chili). In some embodiments of the method, the thioesterase is FATB and it is cloned from a plant of the *Capsicum* genus (e.g., ghost chili).

In some embodiments of the method, the cellular system also comprises a glucose medium for the transformed cellular system. In some embodiments of the method, the cellular system also comprises a pyruvate medium for the transformed cellular system.

In some embodiments of the method, the transformed cellular system further comprises acyl-CoA synthetase. In some embodiments of the method, the transformed cellular system further comprises propionate CoA transferase.

In some embodiments of the method, the transformed cellular system is selected from the group including yeast, non-capsaicinoid producing plants, algae and bacteria. In some embodiments of the method, the cellular system is *E. Coli*. In some embodiments of the method, the cellular system is selected from the group consisting of bacteria, yeast, plant cells, animal cells, an in vitro translation system and a combination thereof. In some embodiments of the method, the transformed cellular system is a microbe culture of yeast or bacteria.

In some embodiments of the method, the 8M is purified. In some embodiments of the method, the 8M is greater than 70% (e.g., greater than 70%, greater than 80%, greater than 90%, greater than 95%, greater than 98%, or greater than 99%) pure. In some embodiments of the method, the 8M content is greater than about 85% (e.g., greater than about 85%, greater than about 90%, greater than about 95%, greater than about 98%, greater than about 99%) by weight on a dry basis.

In some embodiments of the method, step c) comprises: i) purifying crude product; and, ii) removing solvents under vacuum to provide a concentrated capsaicinoid product. In some embodiments of the method, the crude product is purified by column chromatography. In some embodiments of the method, the crude product is purified by acid-base extraction. In some embodiments of the method, the crude product is purified by vacuum distillation. In some embodiments of the method, the crude product is purified by semi-preparative HPLC.

In other aspects the disclosure provides a thioesterase gene having the nucleic acid sequence of SEQ ID NO. 5 or a nucleic acid sequence that is at least 80% (e.g., at least 80%, at least 90%, at least 95%, at least 98%, or at least 99%) identical to SEQ ID NO. 5. In some embodiments, the gene is in a host cell (e.g., a bacteria cell, a yeast cell, a plant cell, or an animal cell). In some embodiments, the gene is in an *E. coli* cell.

In other aspects the disclosure provides a modified KasIIIa gene having the nucleic acid sequence of SEQ ID NO. 6 or a nucleic acid sequence that is at least 80% (e.g., at least 80%, at least 90%, at least 95%, at least 98%, or at least 99%) identical to SEQ ID NO. 6. In some embodiments, the gene is in a host cell (e.g., a bacteria cell, a yeast cell, a plant cell, or an animal cell). In some embodiments, the gene is in an *E. coli* cell.

In other aspects the disclosure provides a modified KasIIIb gene having the nucleic acid sequence of SEQ ID NO. 7 or a nucleic acid sequence that is at least 80% (e.g., at least 80%, at least 90%, at least 95%, at least 98%, or at least 99%) identical to SEQ ID NO. 7. In some embodiments, the gene is in a host cell (e.g., a bacteria cell, a yeast cell, a plant cell, or an animal cell). In some embodiments, the gene is in an *E. coli* cell.

In other aspects the disclosure provides a modified CCL4 gene having the nucleic acid sequence of SEQ ID NO. 8 or a nucleic acid sequence that is at least 80% (e.g., at least 80%, at least 90%, at least 95%, at least 98%, or at least 99%) identical to SEQ ID NO. 8. In some embodiments, the gene is in a host cell (e.g., a bacteria cell, a yeast cell, a plant cell, or an animal cell). In some embodiments, the gene is in an *E. coli* cell.

In other aspects the disclosure provides a modified PCT gene having the nucleic acid sequence of SEQ ID NO. 9 or a nucleic acid sequence that is at least 80% (e.g., at least 80%, at least 90%, at least 95%, at least 98%, or at least 99%) identical to SEQ ID NO. 9. In some embodiments, the gene is in a host cell (e.g., a bacteria cell, a yeast cell, a plant cell, or an animal cell). In some embodiments, the gene is in an *E. coli* cell.

In other aspects, the disclosure provides a Fat2B protein having the amino acid sequence of SEQ ID NO. 2 or an amino acid sequence that is at least 80% (e.g., at least 80%, at least 90%, at least 95%, at least 98%, or at least 99%) identical to SEQ ID NO. 2. In some embodiments, the protein is in a host cell (e.g., a bacteria cell, a yeast cell, a plant cell, or an animal cell). In some embodiments, the protein is in an *E. coli* cell.

In other aspects, the disclosure provides a protein comprising an amino acid sequence derived from the translation the nucleic acid sequence of SEQ ID NO. 5. In some embodiments, the protein is in a host cell (e.g., a bacteria cell, a yeast cell, a plant cell, or an animal cell). In some embodiments, the protein is in an *E. coli* cell.

In other aspects the disclosure provides a biosynthetic method of making a medium chain BCFA (branched-chain fatty acid) comprising (a) expressing KASIIIa, KASIIIb and a thioesterase in a transformed cellular system; (b) producing isobutryl-CoA in the transformed cellular system; and, (c) producing a C8 to C14 branched chain fatty acid. In some embodiments of the method, the branched chain fatty acid produced is used for biofuel production. In some embodiments of the method, the branched chain fatty acid produced is used in biofuel production and has enhanced cold flow properties. In some embodiments of the method, the method further comprises the use of FabH and isobutyl-CoA to produce a fatty acid synthase (FAS) system for elongation of branched chain fatty acids. In some embodiments of the method, the method further comprises the feeding of α-ketoisovalerate or a sodium salt thereof to the transformed cellular system to express 8M. In some embodiments of the method, the method further comprises expressing bkd in the transformed cellular system. In some embodiments of the method, the method further comprises the feeding of isobutyric acid and/or salts thereof to the transformed cellular system to express 8M. In some embodiments of the method, the method further comprises expressing CCL4 in the transformed cellular system. In some embodiments of the method, the method further comprises the feeding of isobutyric acid and/or salts thereof to the transformed cellular system to express 8M. In some embodiments of the method, the method further comprises expressing PCT in the transformed cellular system. In some embodiments of the method, the method further comprises the feeding of isobutyric acid and/or salts thereof to the transformed cellular system to express 8M. In some embodiments of the method, the method further comprises expressing alsS, ilvC, ilvD and bkd in the transformed cellular system.

In some embodiments of the method, the transformed cellular system is selected from the group including yeast, non-capsaicinoid producing plants, algae and bacteria. In some embodiments of the method, the cellular system is *E. Coli*. In some embodiments of the method, the cellular system is selected from the group consisting of bacteria, yeast, plant cells, animal cells, an in vitro translation system and a combination thereof. In some embodiments of the method, the transformed cellular system is a microbe culture of yeast or bacteria. In some embodiments of the method, the branched chain fatty acid and/or 8M is purified.

In some embodiments of the method, the branched chain fatty acid and/or 8M is greater than 70% (e.g., greater than 70%, greater than 80%, greater than 90%, greater than 95%, greater than 98%, or greater than 99%) pure. In some embodiments of the method, the branched chain fatty acid and/or 8M content is greater than about 85% (e.g., greater than about 85%, greater than about 90%, greater than about 95%, greater than about 98%, greater than about 99%) by weight on a dry basis.

In some embodiments of the method, step c) comprises: i) purifying crude product; and, ii) removing solvents under vacuum to provide a concentrated branched chain fatty acid and/or 8M product. In some embodiments of the method, the crude product is purified by column chromatography. In some embodiments of the method, the crude product is purified by acid-base extraction. In some embodiments of the method, the crude product is purified by vacuum distillation. In some embodiments of the method, the crude product is purified by semi-preparative HPLC.

As for the cellular system, in some embodiments, it is selected from the group consisting of bacteria, yeast, and a combination thereof, or any cellular system that would allow the genetic transformation with the selected genes and thereafter the biosynthetic production of the desired 8-methyl nonanoic acid from a feeding of glucose (de novo pathway) or isobutyric acid (ACS or PCT pathway) precursors. In a most preferred microbial system, *E. coli* is used to produce the desired 8M.

While the disclosure is susceptible to various modifications and alternative forms, specific embodiments thereof are shown by way of example in the drawings and will herein be described in detail. It should be understood, however, that the drawings and detailed description presented herein are not intended to limit the disclosure to a particular embodiment disclosed, but on the contrary, the intention is to cover all modifications, equivalents, and alternatives falling within the spirit and scope of the present disclosure as defined by the appended claims.

Other features and advantages of this invention will become apparent in the following detailed description of preferred embodiments of this invention, taken with reference to the accompanying drawings.

DESCRIPTION OF THE PREFERRED EMBODIMENT

Explanation of Terms Used Herein

Figure 1:
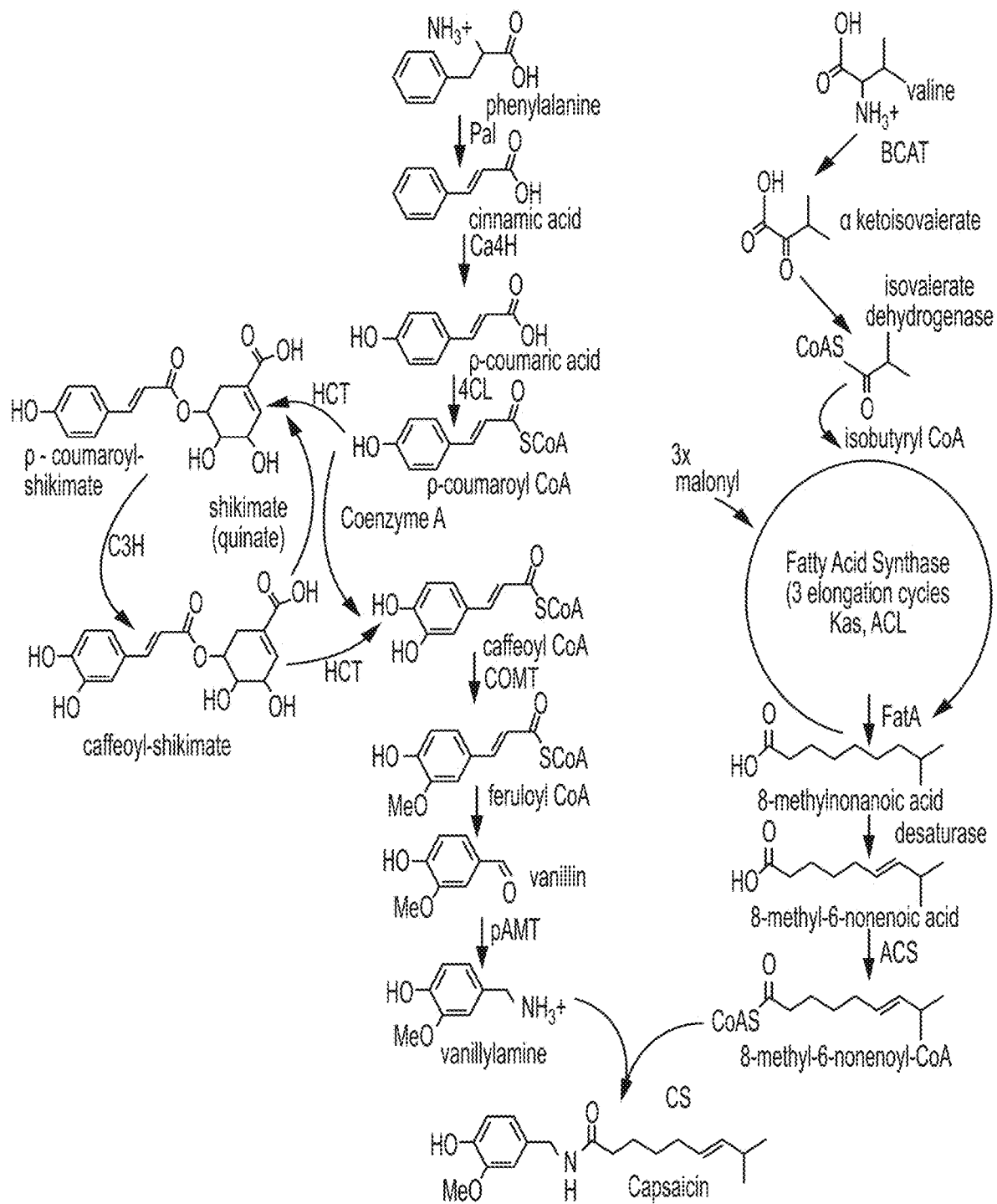
FIG. 1. The Capsaicinoid Biosynthetic Pathway. The aminotransferase (pAMT) catalyzes the formation of vanillyamine from vanillin. Pal, phenylalanine ammonia lyase; Ca4H, cinnamic acid 4-hydroxylase; 4CL, 4-coumarate CoA ligase; HCT, hydroxycinnamoyl transferase; C3H, coumaroyl shikimate/quinate 3-hydroxylase; COMT, caffeic acid O-methyltransferase; pAMT, aminotransferase; BCAT, branched-chain amino acid transferase; Kas, 3-keto-acyl ACP synthase; ACL, acyl carrier protein; Fat, acyl-ACP thioesterase; ACS, acyl-CoA synthetase; CS, capsaicin synthase (Stewart C et al. 2007, J. Exp. Bot. 58:979-991).

Capsaicin or CP is a colorless irritant phenolic amide $C_{18}H_{27}NO_3$ and is one of a series of phenolic amides found in various *Capsicum* species and hybrids thereof that gives hot peppers their hotness or pungency and that is used for food, medicine, and security applications. Pure CP is a volatile, hydrophobic, colorless, odorless, crystalline to waxy compound.

Capsaicinoid as used herein this refers to a class of irritant compounds, related to Capsaicin, that are responsible for the heat of chili peppers. They are irritants for mammals, including humans, and produce a sensation of burning in any tissue with which they come into contact. The capsaicinoids including 8M are produced as secondary metabolites by chili peppers, probably as deterrents against certain mammals and fungi.

Cellular system is any cells that provide for the expression of ectopic proteins. It includes bacteria, yeast, plant cells and animal cells. It includes both prokaryotic and eukaryotic cells. It also includes the in vitro expression of proteins based on cellular components, such as ribosomes.

Fatty Acids, C8-C14. According to the current disclosure a variety of fatty acids can be used as starting source materials. The source materials include vanillin, vanillylamine or their derivatives with modifications at the aromatic ring such as methylation, ethylation, or glycosylation; and more particularly 8-14 carbon straight chain or branched chain fatty acids or their derivatives such as hydroxy fatty acids (Ex: Octanoic acid; Nonanoic acid; Decanoic acid; Undecanoic acid; and, Dodecanoic acid) can be straight chain fatty acids or branched chain fatty acids and be used to make the 8-methyl nonanoic acid of the current disclosure.

Growing the Cellular System. Growing includes providing an appropriate medium that would allow cells to multiply and divide. It also includes providing resources so that cells or cellular components can translate and make recombinant proteins.

Protein Expression. Protein production can occur after gene expression. It consists of the stages after DNA has been transcribed to messenger RNA (mRNA). The mRNA is then translated into polypeptide chains, which are ultimately folded into proteins. DNA is present in the cells through transfection—a process of deliberately introducing nucleic acids into cells. The term is often used for non-viral methods in eukaryotic cells. It may also refer to other methods and cell types, although other terms are preferred: "transformation" is more often used to describe non-viral DNA transfer in bacteria, non-animal eukaryotic cells, including plant cells. In animal cells, transfection is the preferred term as transformation is also used to refer to progression to a cancerous state (carcinogenesis) in these cells. Transduction is often used to describe virus-mediated DNA transfer. Transformation, transduction, and viral infection are included under the definition of transfection for this application.

Yeast. According to the current disclosure yeast as claimed herein are eukaryotic, single-celled microorganisms classified as members of the fungus kingdom. Yeast are unicellular organisms which evolved from multicellular ancestors but with some species useful for the current disclosure being those that can develop multicellular characteristics by forming strings of connected budding cells known as pseudo hyphae or false hyphae.

Acronyms

AAE, acyl activating enzyme
PCT, propionate/isobutyrate-CoA transferase
TE, acyl-ACP thioesterase
Pal, phenylalanine ammonia lyase;
Ca4H, cinnamic acid 4-hydroxylase;
4CL, 4-coumarate CoA ligase;
HCT, hydroxycinnamoyl transferase;
C3H, coumaroyl shikimate/quinate 3-hydroxylase;
COMT, caffeic acid O-methyltransferase; pAMT, aminotransferase;
BCAT, branched-chain amino acid transferase;
KAS, 3-keto-acyl ACP synthase;
ACL, acyl carrier protein;
FatA, acyl-ACP thioesterase;
ACS, acyl-CoA synthetase; and,
CS, capsaicin synthase.

DETAILED DESCRIPTION

The present disclosure provides, in part, a microbial fermentation system for the production of 8M.

Due to the low-temperature operability of branched-chain fatty acids which are superior to straight chain fuels, several microbial fermentation processes for the production of branched long-chain fatty acids have been described in the field of biofuel research (Howard et al. 2013; Haushalter et al. 2014; Jiang et al. 2015; Tao et al. 2015; Bentley et al. 2016). However, there has been no report on branched medium-chain fatty acid production using microbial fermentation.

As shown in FIG. 1, an acyl-ACP thioesterase controls the chain length of fatty acid and is one of the key enzymes in 8M biosynthetic pathway. However, such an 8M-specific thioesterase has not been characterized so far. Alum et al. (2003), based on differential expression, once isolated FatA gene (GenBank: AF318288.1) from pepper fruits and people tend to believe this thioesterase is involved in 8M biosynthesis (FIG. 1, Stewart et al. 2007). However, the biochemical activity of FatA has not been reported so far. Using bioinformatics tools, Mazourek et al. (2009) isolated another acyl-ACP thioesterase, FatB (GenBank: EU616562) from hot peppers. However, FatB has not been characterized so far and its role in 8M biosynthesis is still unknown. In this application, we reported the identification of the third acyl-ACP thioesterase gene from the genome of *C. annuum* L_Zunla-1 (Qin et al. 2014) and named it as FatB2 (NCBI Reference Sequence: XM_016708605.1). FatB2 has 372 aa which contains 64 aa of signal peptide for chloroplast targeting. (See SEQ IDS NOs 1 through 5).

Figure 8:
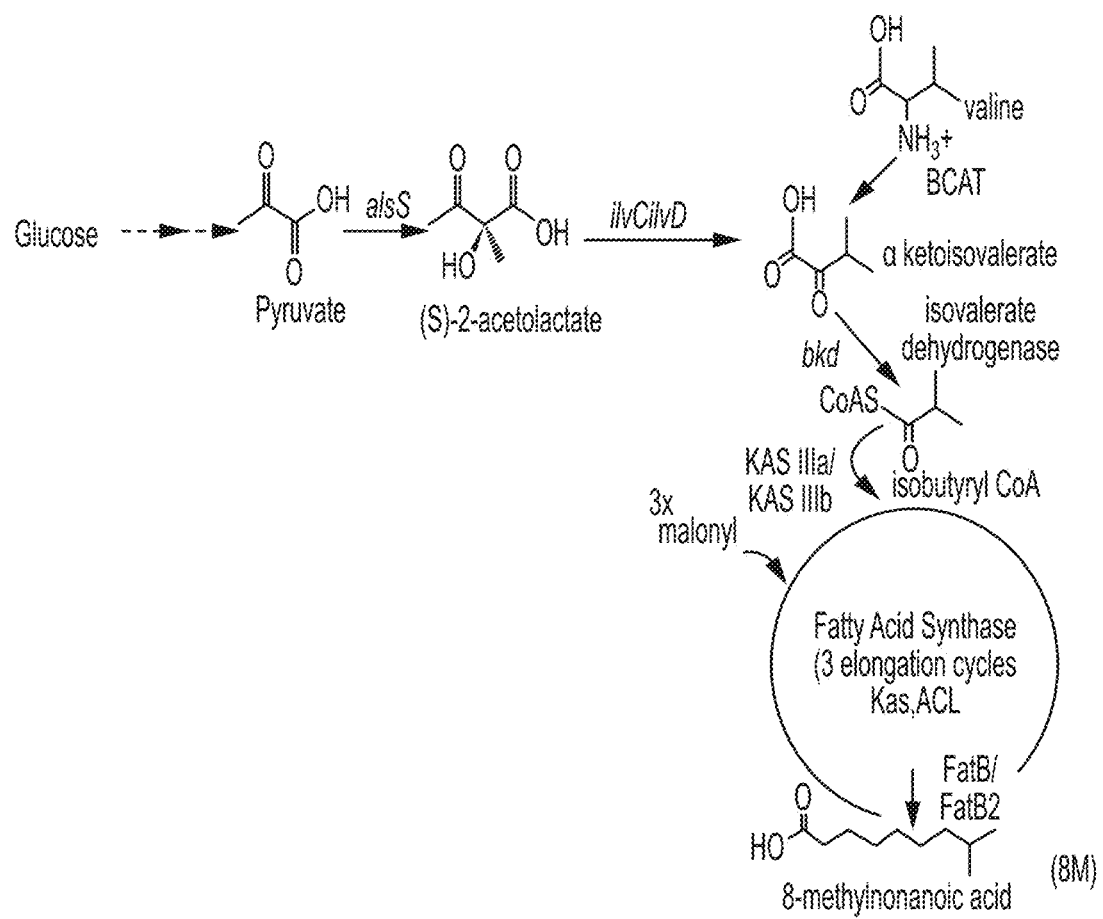
FIG. 8. De Novo production of 8M in *E. coli*. De Novo production of 8M in *E. coli*. Colored genes are those engineered ones. alsS and bkd are from *Bacillus subtilis* 168; ilvC and ilvD are from *E. coli*; KAS IIIa/KAS IIIb and FatB/FatB2 are from hot peppers. This figure was adapted from FIG. 1 of Jiang et al. (2015). (See SEQ IDS NOs 1 through 7).

The 8M produced herein was synthesized in modified *E. coli* cultures that were modified to carry the KASIIIa/KASIIIb and FatB/FatB2 genes from hot peppers and other genes related to the production of isobutyryl-CoA. (See SEQ IDS NOs 1 through 6). Isobutyryl-CoA could be generated de novo from glucose by the overexpression of alsS, ilvC, ilvD and bkd genes. Alternatively, isobutyryl-CoA could be produced from fed isobutyric acid by the overexpression of an ACS (isobutyryl-CoA synthetase) or a PCT (propionate CoA-transferase) gene. These genes allowed the properly fed selected strains to synthesize the 8-methyl nonanoic acid (FIG. 8).

Organic or non-biological processes for the synthesis of capsaicin and analogues thereof have been reported, for example, by Crombie et al., (J. CHEM SOC., 1025-27 (1955)) describes an inorganic synthesis of capsaicin, N-(4-hydroxy-3-methoxybenzyl)-8-methylnon-trans-6-enamide, the active principle in red pepper. Other organic pathways have been shown in U.S. Pat. No. 4,493,848 issued to LaHann et al., and U.S. Pat. No. 5,094,782 issued to Chen et al.

Capsaicinoids, have long been used as an experimental tool because of their selective action on the small diameter afferent nerve fibers C-fibers and A-delta fibers that are believed to signal pain. From studies in animals, capsaicinoids appears to trigger C-fiber membrane depolarization by opening cation channels permeable to calcium and sodium. Recently one of the receptors for capsaicinoid effects has been cloned.

In most chili peppers, vanillylamine is formed from phenylalanine via ferulic acid, vanillin and related compounds, and capsaicinoid is produced from vanillyamine and branched chain fatty acid by capsaicin synthase (FIG. 1).

Synthetic Biology

Genetically engineered microbes have become an increasingly important platform for the production of drugs, chemicals, and biofuels from renewable resources (Du et al., 2011). These biotechnological products, when used in food, can be labeled 'natural' in food sector according to current regulations (Häusler and Münch, 1997).

Exemplary capsaicinoids include, but are not limited to: nonivamide, N-vanillylnonanamides, N-vanillylsulfonamides, N-vanillylureas, N-vanillylcarbamates, N[(substituted phenyl)methyl]alkylamides, methylene substituted N[(substituted phenyl)methyl]alkanamides, N[(substituted phenyl)methyl]-cis-monosaturated alkenamides, N[(substituted phenyl)methyl]diunsaturated amides, 8M, 3-hydroxyacetanilide, hydroxyphenylacetamides, pseudocapsaicin, dihydrocapsaicin, nordihydrocapsaicin, homocapsaicin, homodihydrocapsaicin I, anandamide, piperine, zingerone, warburganal, polygodial, aframodial, cinnamodial, cinnamosmolide, cinnamolide, civamde, nonivamide, olvanil, N-oleyl-homovanillamidia, isovelleral, scalaradial, ancistrodial, and any combinations or mixtures thereof.

Determination of Sequence Similarity Using Hybridization Techniques

Nucleic acid hybridization is a technique well known to those of skill in the art of DNA manipulation. The hybridization properties of a given pair of nucleic acids are an indication of their similarity or identity.

The term "hybridization" refers generally to the ability of nucleic acid molecules to join via complementary base strand pairing. Such hybridization may occur when nucleic acid molecules are contacted under appropriate conditions. "Specifically hybridizes" refers to the ability of two nucleic acid molecules to form an anti-parallel, double-stranded nucleic acid structure. A nucleic acid molecule is said to be the "complement" of another nucleic acid molecule if they exhibit "complete complementarity," i.e., each nucleotide in one sequence is complementary to its base pairing partner nucleotide in another sequence. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Nucleic acid molecules that hybridize to other nucleic acid molecules, e.g., at least under low stringency conditions are said to be "hybridizable cognates" of the other nucleic acid molecules. Conventional low stringency and high stringency conditions are described herein and by Sambrook et al., MOLECULAR CLONING, A LABORATORY MANUAL, 2nd Ed., Cold Spring Harbor Press, Cold Spring Harbor, N.Y. (1989) and by Haymes et al., NUCLEIC ACID HYBRIDIZATION, A PRACTICAL APPROACH, IRL Press, Washington, D.C. (1985). Departures from complete complementarity are permissible, as long as such departures do not completely preclude the capacity of the molecules to form a double-stranded structure.

Low stringency conditions may be used to select nucleic acid sequences with lower sequence identities to a target nucleic acid sequence. One may wish to employ conditions such as about 0.15 M to about 0.9 M sodium chloride, at temperatures ranging from about 20° C. to about 55° C. High stringency conditions may be used to select for nucleic acid sequences with higher degrees of identity to the disclosed nucleic acid sequences (Sambrook et al., 1989). High stringency conditions typically involve nucleic acid hybridization in about 2× to about 10×SSC (diluted from a 20×SSC stock solution containing 3 M sodium chloride and 0.3 M sodium citrate, pH 7.0 in distilled water), about 2.5× to about 5×Denhardt's solution (diluted from a 50× stock solution containing 1% (w/v) bovine serum albumin, 1% (w/v) ficoll, and 1% (w/v) polyvinylpyrrolidone in distilled water), about 10 mg/mL to about 100 mg/mL fish sperm DNA, and about 0.02% (w/v) to about 0.1% (w/v) SDS, with an incubation at about 50° C. to about 70° C. for several hours to overnight. High stringency conditions are preferably provided by 6×SSC, 5×Denhardt's solution, 100 mg/mL fish sperm DNA, and 0.1% (w/v) SDS, with an incubation at 55° C. for several hours. Hybridization is generally followed by several wash steps. The wash compositions generally comprise 0.5× to about 10×SSC, and 0.01% (w/v) to about 0.5% (w/v) SDS with a 15 minute incubation at about 20° C. to about 70° C. Preferably, the nucleic acid segments remain hybridized after washing at least one time in 0.1×SSC at 65° C.

Analysis of Sequence Similarity Using Identity Scoring

As used herein "sequence identity" refers to the extent to which two optimally aligned polynucleotide or peptide sequences are invariant throughout a window of alignment of components, e.g., nucleotides or amino acids. An "identity fraction" for aligned segments of a test sequence and a reference sequence is the number of identical components which are shared by the two aligned sequences divided by the total number of components in reference sequence segment, i.e., the entire reference sequence or a smaller defined part of the reference sequence.

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned (with appropriate nucleotide insertions, deletions, or gaps totaling less than 20 percent of the reference sequence over the window of comparison). Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and preferably by computerized implementations of these algorithms such as GAP, BESTFIT, FASTA, and TFASTA available as part of the GCG® Wisconsin Package® (Accelrys Inc., Burlington, Mass.). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this disclosure "percent identity" may also be determined using BLASTX version 2.0 for translated nucleotide sequences and BLASTN version 2.0 for polynucleotide sequences.

The percent of sequence identity is preferably determined using the "Best Fit" or "Gap" program of the Sequence Analysis Software Package™ (Version 10; Genetics Computer Group, Inc., Madison, Wis.). "Gap" utilizes the algorithm of Needleman and Wunsch (Needleman and Wunsch, JOURNAL OF MOLECULAR BIOLOGY 48:443-453, 1970) to find the alignment of two sequences that maximizes the number of matches and minimizes the number of gaps. "BestFit" performs an optimal alignment of the best segment of similarity between two sequences and inserts gaps to maximize the number of matches using the local homology algorithm of Smith and Waterman (Smith and Waterman, ADVANCES IN APPLIED MATHEMATICS, 2:482-489, 1981, Smith et al., NUCLEIC ACIDS RESEARCH 11:2205-2220, 1983). The percent identity is most preferably determined using the "Best Fit" program.

Useful methods for determining sequence identity are also disclosed in the Basic Local Alignment Search Tool (BLAST) programs which are publicly available from National Center Biotechnology Information (NCBI) at the National Library of Medicine, National Institute of Health, Bethesda, Md. 20894; see BLAST Manual, Altschul et al., NCBI, NLM, NIH; Altschul et al., J. MOL. BIOL. 215:403-410 (1990); version 2.0 or higher of BLAST programs allows the introduction of gaps (deletions and insertions) into alignments; for peptide sequence BLASTX can be used to determine sequence identity; and, for polynucleotide sequence BLASTN can be used to determine sequence identity.

As used herein, the term "substantial percent sequence identity" refers to a percent sequence identity of at least about 70% sequence identity, at least about 80% sequence identity, at least about 85% identity, at least about 90% sequence identity, or even greater sequence identity, such as about 98% or about 99% sequence identity. Thus, one embodiment of the disclosure is a polynucleotide molecule that has at least about 70% sequence identity, at least about 80% sequence identity, at least about 85% identity, at least about 90% sequence identity, or even greater sequence identity, such as about 98% or about 99% sequence identity with a polynucleotide sequence described herein. Polynucleotide molecules that have the activity of the ACS and CS genes of the current disclosure are capable of directing the production of a variety of capsaicinoids and have a substantial percent sequence identity to the polynucleotide sequences provided herein and are encompassed within the scope of this disclosure.

"Homology" refers to the level of similarity between two or more nucleic acid or amino acid sequences in terms of percent of positional identity (i.e., sequence similarity or identity). Homology also refers to the concept of similar functional properties among different nucleic acids or proteins.

In an alternative embodiment, the nucleic acid molecule comprises a nucleic acid sequence that exhibits 70% or greater identity, and more preferably at least 80 or greater, 85 or greater, 87 or greater, 88 or greater, 89 or greater, 90 or greater, 91 or greater, 92 or greater, 93 or greater, 94 or greater, 95 or greater, 96 or greater, 97 or greater, 98 or greater, or 99% or greater identity to a nucleic acid molecule selected from the group consisting of SEQ ID NO: 1 through and SEQ ID NO: 9 or any other nucleic acid sequence described herein, any complements thereof, any fragments thereof, or any cis elements thereof. The nucleic acid molecule preferably comprises a nucleic acid sequence that exhibits a 75% or greater sequence identity with a polynucleotide selected from the group consisting of SEQ ID NO: 1 through and SEQ ID NO: 9 or any other nucleic acid sequence described herein, any complements thereof, any fragments thereof, or any cis elements thereof. The nucleic acid molecule more preferably comprises a nucleic acid sequence that exhibits an 80% or greater sequence identity with a polynucleotide selected from the group consisting of SEQ ID NO: 1 through SEQ ID NO: 9 or any other nucleic acid sequence described herein, any complements thereof, any fragments thereof, or any cis elements thereof. The nucleic acid molecule most preferably comprises a nucleic acid sequence that exhibits an 85% or greater sequence identity with a polynucleotide selected from the group consisting of SEQ ID NO: 1 through SEQ ID NO: 9 or any other nucleic acid sequence described herein, any complements thereof, any fragments thereof, or any cis elements thereof.

For purposes of this disclosure "percent identity" may also be determined using BLASTX version 2.0 for translated nucleotide sequences and BLASTN version 2.0 for polynucleotide sequences. In a preferred embodiment of the present disclosure, the presently disclosed corn genomic promoter sequences comprise nucleic acid molecules or fragments having a BLAST score of more than 200, preferably a BLAST score of more than 300, and even more preferably a BLAST score of more than 400 with their respective homologues.

According to another embodiment of the current disclosure the efficiency of heterologous protein production in a microbial system can be enhanced by codon changes that alter the DNA sequences to one that may be preferred by the cellular system being used for expression but that varies from the original gene source organism without changing the eventual polypeptide produced. Approaches normally used to overcome this problem include targeted mutagenesis to remove rare codons or the addition of rare codon tRNAs in specific cell lines to move towards a codon sequence preferred by a host organism that will produce the polypeptide of interest. Recently, improvements in such "codon optimization" technology have enabled cost-effective production of synthetic genes, making this a feasible alternative and potentially useful for the current disclosure.

Identity and Similarity

Identity is the fraction of amino acids that are the same between a pair of sequences after an alignment of the sequences (which can be done using only sequence information or structural information or some other information, but usually it is based on sequence information alone), and similarity is the score assigned based on an alignment using some similarity matrix. The similarity index can be any one of the following BLOSUM62, PAM250, or GONNET, or any matrix used by one skilled in the art for the sequence alignment of proteins.

Identity is the degree of correspondence between two sub-sequences (no gaps between the sequences). An identity of 25% or higher implies similarity of function, while 18-25% implies similarity of structure or function. Keep in mind that two completely unrelated or random sequences (that are greater than 100 residues) can have higher than 20% identity. Similarity is the degree of resemblance between two sequences when they are compared. This is dependent on their identity.

As is evident from the foregoing description, certain aspects of the present disclosure are not limited by the details of the examples illustrated herein, and it is therefore contemplated that other modifications and applications, or equivalents thereof, will occur to those skilled in the art. It is accordingly intended that the claims shall cover all such modifications and applications that do not depart from the spirit and scope of the present disclosure.

Moreover, unless defined otherwise, all technical and scientific terms used herein have the same meaning as commonly understood by one of ordinary skill in the art to which the disclosure belongs. Although any methods and materials similar to or equivalent to or those described herein can be used in the practice or testing of the present disclosure, the preferred methods and materials are described above.

Although the foregoing invention has been described in some detail by way of illustration and example for purposes of understanding, it will be apparent to those skilled in the art that certain changes and modifications may be practiced. Therefore, the description and examples should not be construed as limiting the scope of the invention, which is delineated by the appended claims.

Accordingly, it is to be understood that the embodiments of the invention herein providing for the production of 8-methyl nonanoic acid is illustrative of the application of the principles of the invention. It will be evident from the foregoing description that changes in the form, methods of use, and applications of the elements of the disclosed production methods and selected microbial strains may be resorted to without departing from the spirit of the invention, or the scope of the appended claims.

EXAMPLES

Example 1

Cloning and Characterization of Different Pathways

Previously, an *E. coli* fermentation platform was developed where various capsaicinoids could be produced upon the feeding of fatty acids and vanillylamine/vanillin (Chen et al. 2015). The production of nonivamide was also demonstrated by this system. In the current disclosure, this system was used to fully sequence and characterize three *Capsicum* acyl-ACP thioesterases and thereby elucidate their roles in 8M biosynthesis. To facilitate their expression in *E. coli*, the nucleotide sequences encoding the matured proteins without transient peptides were codon optimized against *E. coli* genome and synthesized by GenScript (Piscataway, N.J.).

The synthesized genes were cloned into pCDFDuet-1 vector (Spect+) and transformed into BL21(DE3) for both in vitro and in vivo studies.

Figure 2:
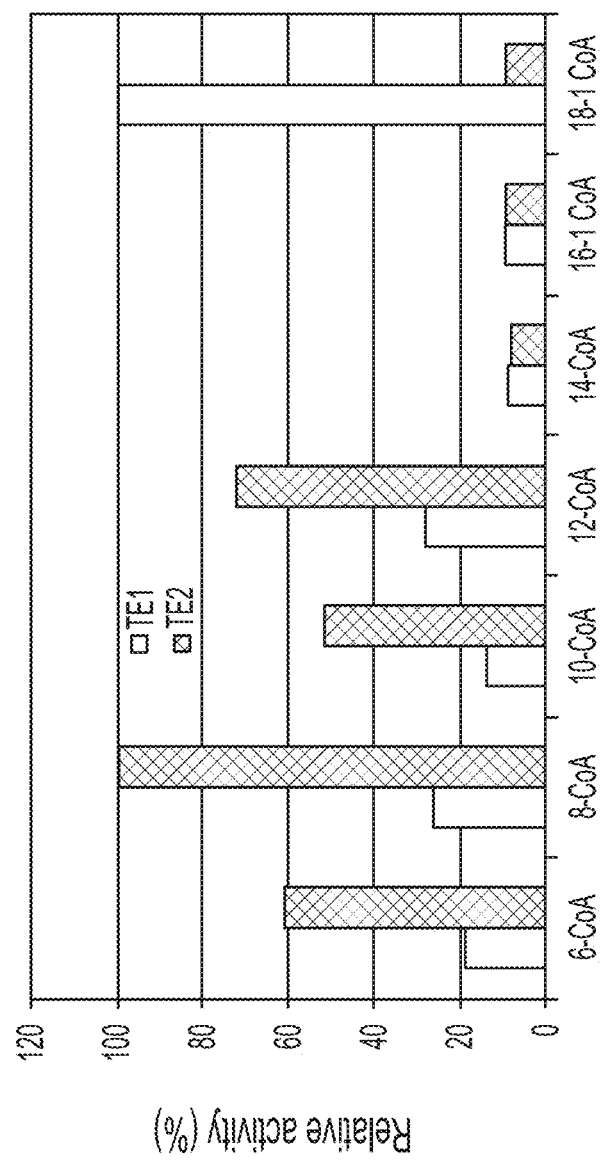
FIG. 2. The activities of purified FatA (TE1, left bar of each pair of bars) and FatB (TE2, right bar of each pair of bars) proteins against various acyl-CoAs. Acyl-CoAs were purchased from Sigma (St Louis, Mo.). The activity of thioesterase (TE) was assayed in 100 mM Tris buffer, pH7.5 containing 100 mg/L of acyl-CoA and 5 μl of purified enzyme at 30° C. Free CoA and acyl-CoAs were analyzed by HPLC. HPLC was performed with Dionex-UltiMate® 3000 LC Systems (Thermo Scientific) using an Acclaim® 120 CI 8 reversed-phase column (Thermo Scientific; 3μ, 120 A, 150 χ 3 mm). The mobile phase consisted of solvent A (0.1% trifluoroacetic acid) and solvent B (acetonitrile). The gradient elution procedure was as follows: 0 to 5 min, 5% of B; 5 to 9 min, a linear gradient from 5 to 80% of B; 9 to 11 min, 80% of B; 11 to 12 min, 5% of B. The flow rate was 0.6 ml/min. The diode array detector collected data in the 200- to 400-nm range. For detection and quantification of substrate and products, peak areas were measured at 257 nm. Due to the unavailability of commercial acyl-ACPs, various acyl-CoAs from Sigma were used as the substrates of thioesterases.
Figure 3:
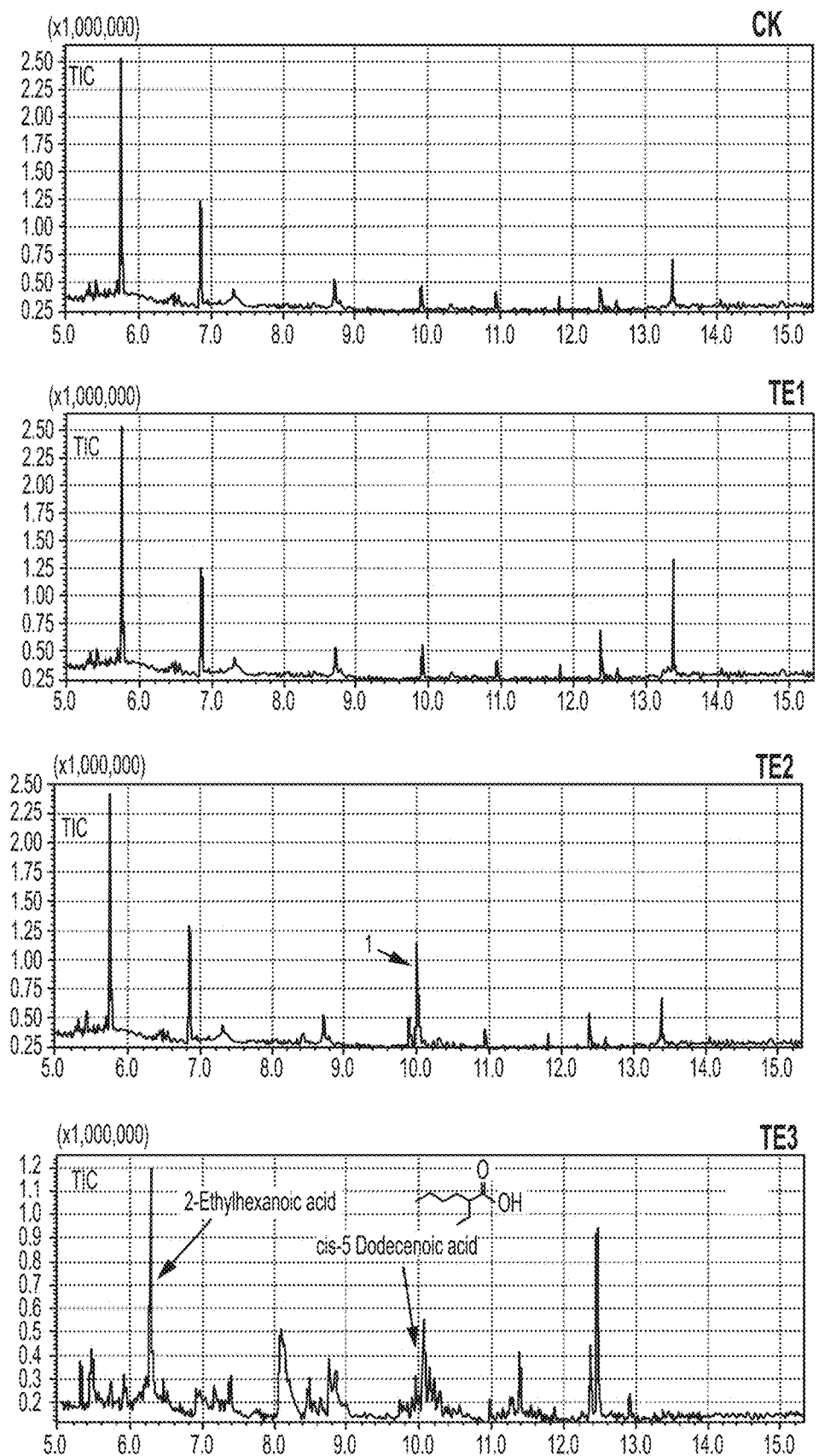
FIG. 3. GC/MS analysis of supernatants from IPTG-induced BL21(DE3) cultures. GC/MS analysis of supernatants from IPTG-induced BL21(DE3) cultures. CK, BL21 (DE3) with the empty vector; TE1, FatA; TE2, FatB; TE3, FatB2. The cultures were grown at 16° C. after the induction by 1 mM IPTG and one day later, fatty acids were extracted from the supernatants.
Figure 4:
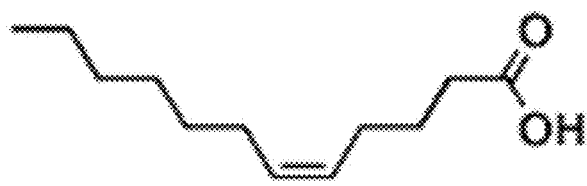
FIG. 4. Cis-5-dodecenoic acid (CAS No. 2430-94-6).

As shown in FIG. 2, FatA (TE1 in FIG. 2) is a long chain acyl-CoA thioesterase whereas FatB prefers medium chain acyl-CoAs (TE2 in FIG. 2). It seems that FatB rather than FatA is involved in 8M biosynthesis. This conclusion is supported by the analysis of fatty acid composition in cell cultures (FIG. 3). Peak 1 was identified as cis-5 dodecenoic acid (FIG. 4) by the comparison of this retention time and mass spectrum with that of cis-5 dodecenoic acid standard from Sigma. As shown in FIG. 3, cis-5-dodecenoic acid is produced by FatB and FatB2 confirming involvement in 8M production.

In plants as well as in bacteria, KAS III (β-ketoacyl-ACP synthase III, FabH) catalyzes the condensation of acetyl-CoA and malonyl-CoA, an initial step in fatty acid biosynthetic pathway whereas KAS I is involved in fatty acid elongation. In 8M biosynthetic pathway, a KAS III enzyme must be able to accept isobutyryl-CoA as a substrate (FIG. 1). However, such an enzyme has not been identified in the plant kingdom although the bacterial KASIII enzymes using isobutyryl-CoA as a substrate have been well characterized (Howard et al. 2013; Haushalter et al. 2014; Jiang et al. 2015; Tao et al. 2015; Bentley et al. 2016).

Using a bioinformatics approach, Mazourek et al. (2009) isolated KAS IIIa (EU616569) and KAS IIIb (EU616570) genes from hot peppers. However, their enzyme activity and roles in 8M biosynthesis have not been reported. In the present disclosure, these two KAS III enzymes were characterized in order to understand their roles in 8M biosynthesis. To facilitate their expression in *E. coli*, the nucleotide sequences encoding the matured proteins without transient peptides were codon optimized against *E. coli* genome and synthesized by GenScript (SEQ ID. NOS 6 and 7, respectively). The synthesized genes were cloned into pRSFDuet-1 vector (Kan+) and transformed into BL21(DE3) containing pCDFDuet-FatB or pCDFDuet-FatB2 for in vivo studies.

Figure 5:
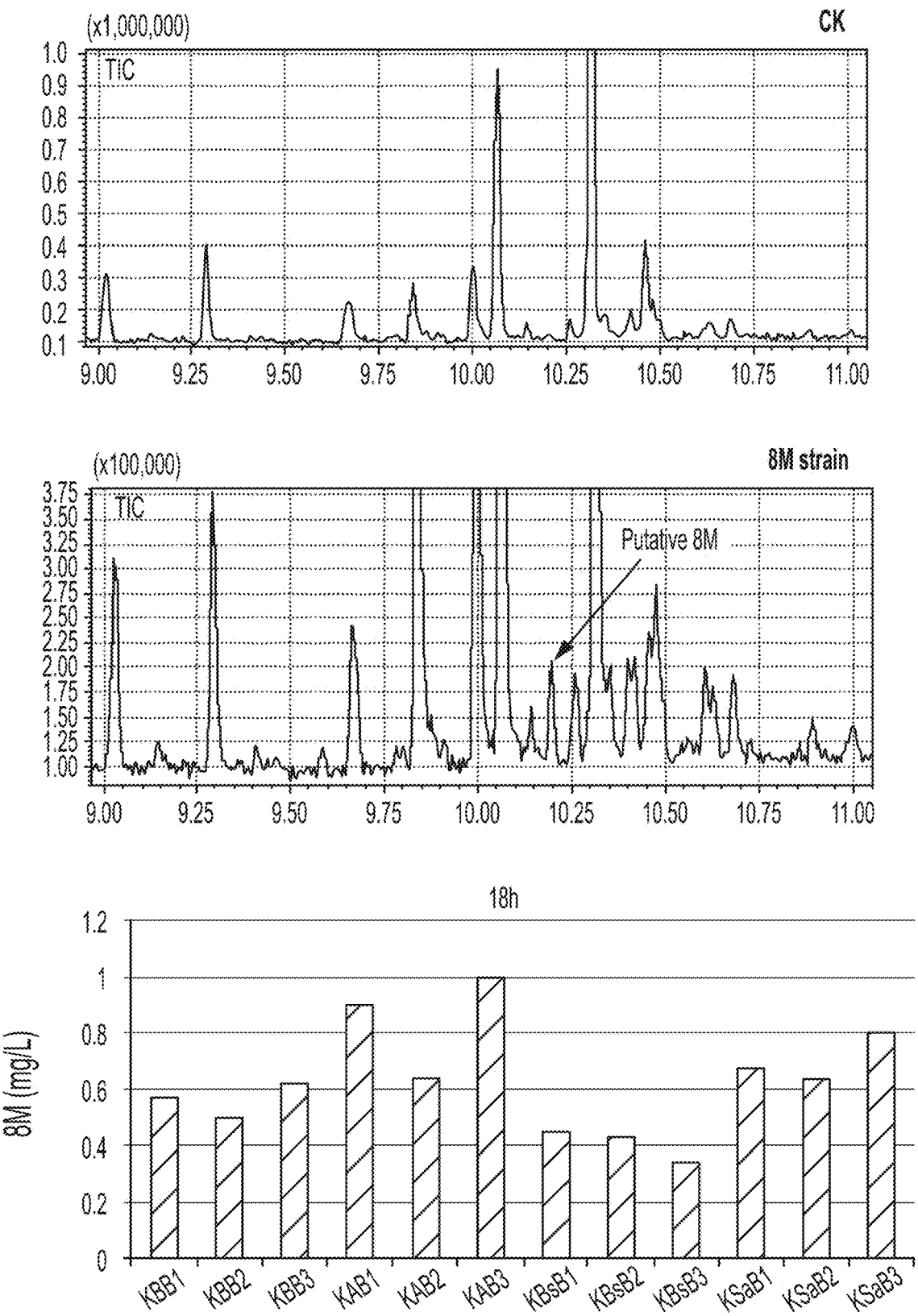
FIG. 5. Production of 8M in strains with different FabH genes. KBB, KAS IIIb; KAB, KAS Ma; KBsB1, FabH2 from *Bacillus subtilis* 168; KSaB, FabH from *Staphylococcus aureus*. KBsB and KSaB are two positive controls (Jiang et al. 2015). The experiment was performed in triplicate.
Figure 6:
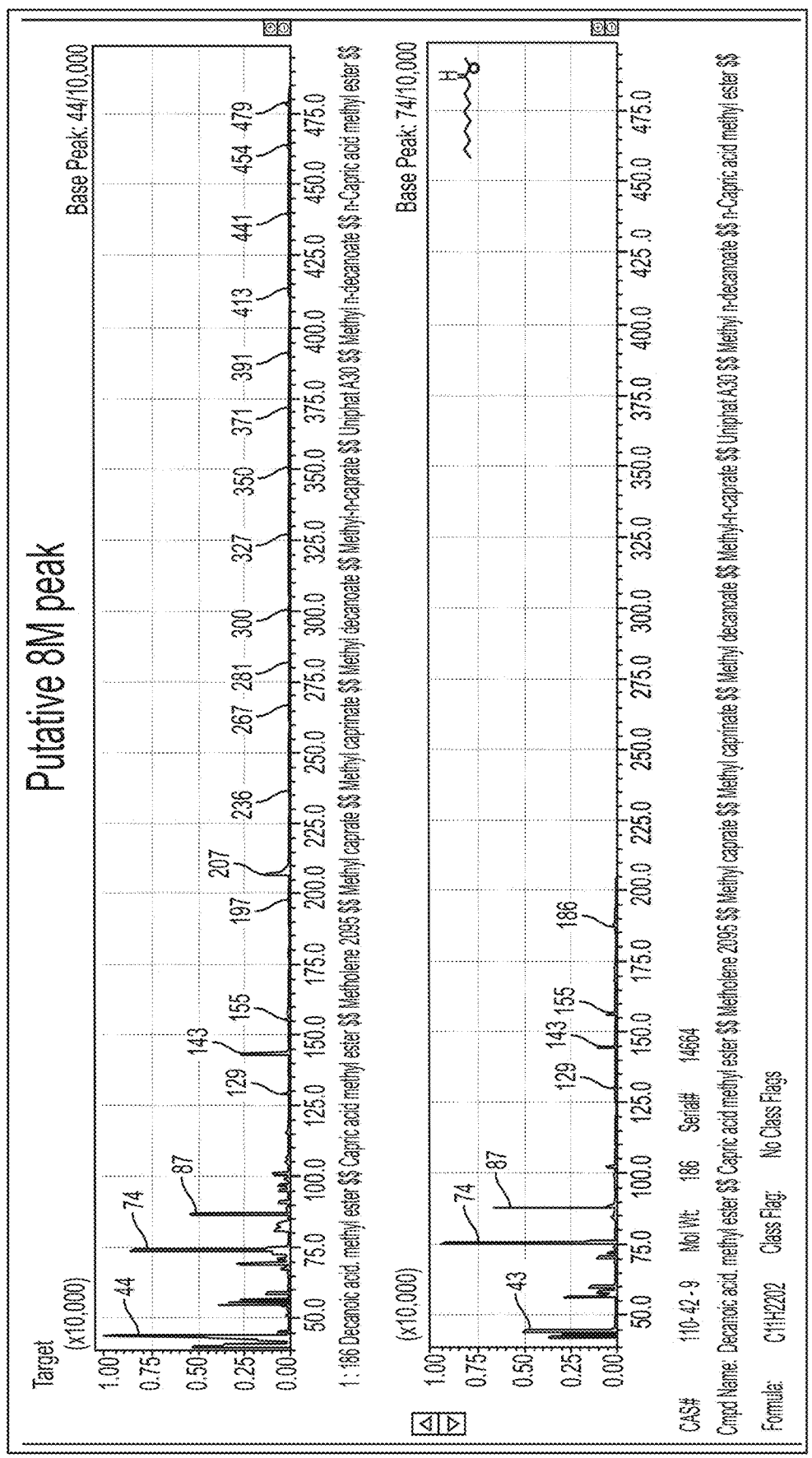
FIG. 6. MS spectra of putative 8M peak and 8M standard and GC profile of 8M Standard. The lower spectrum is the library match.
Figure 6:
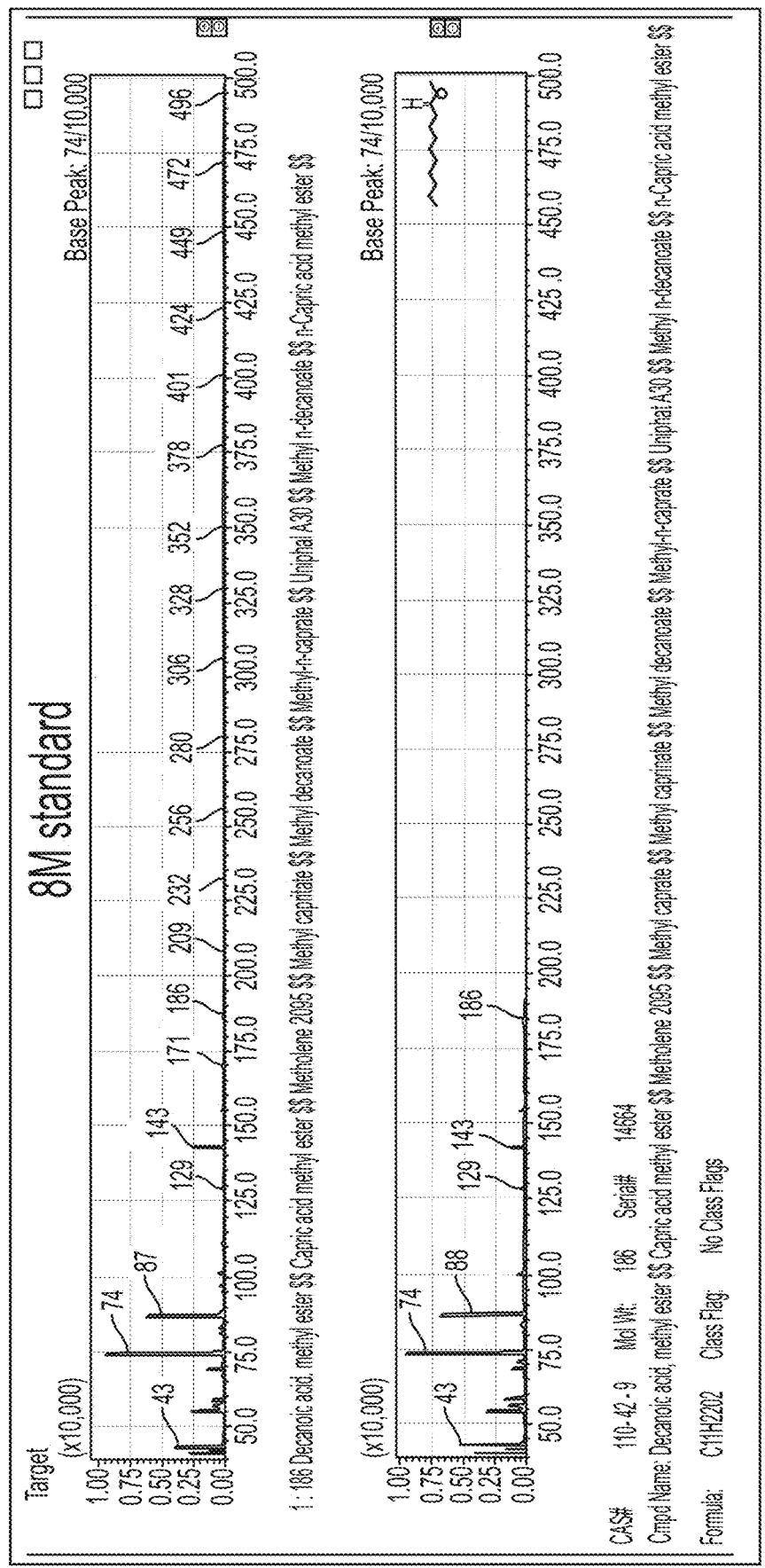
Figure 6:
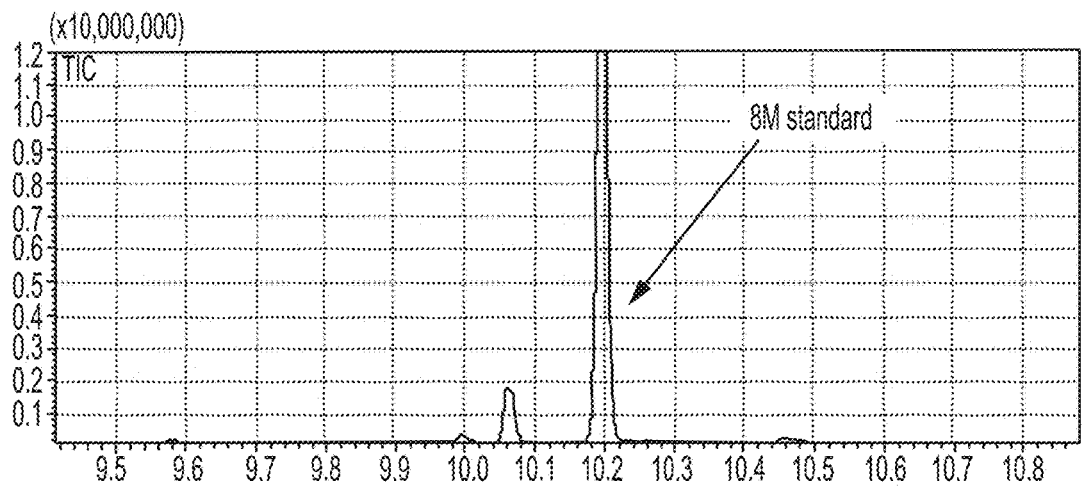

However, when KAS IIIa/KAS IIIb co-expressed with FatB/FatB2 in BL21(DE3) cells, upon the induction by 1 mM IPTG, no 8M was produced (data not shown), suggesting that the endogenous isobutyryl-CoA concentration might be too low to support 8M biosynthesis. The bkd operon was cloned from the genome of *Bacillus subtilis* 168 which encode an ketoisovalerate dehydrogenase (FIG. 1) into pET-Duet-1 vector (AMP+) and bkd was co-expressed with KAS IIIa/KAS IIIb and FatB/FatB2 in BL21(DE3). After IPTG-induction, upon the feeding of 1 g/L of α-ketoisovalerate (FIG. 1), 8M was produced (FIGS. 5 and 6).

Figure 7:
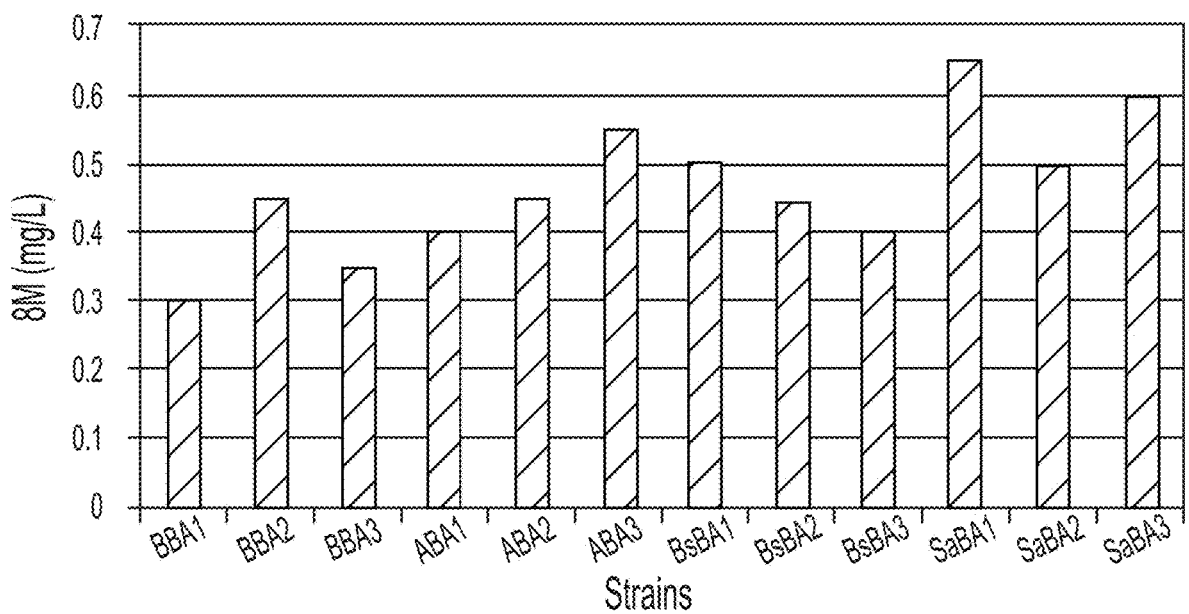
FIG. 7. Production of 8M in strains with CCL4, FaB2 and different FabH genes. BBA, KAS IIIb; ABA, KAS Ma; BsBA1, FabH2 from *Bacillus subtilis* 168; SaBA, FabH from *Staphylococcus aureus*. The experiment was performed in triplicate.

In another example, the CCL4 gene (GenBank: AGA17921.1) from *Humulus lupulus* was synthesized with codon optimization against *E. coli* genome. CCL4 encodes an isobutyryl-CoA synthetase which converts isobutyric acid into isobutyryl-CoA (Xu et al., 2013). CCL4 was cloned into pETDuet-1 vector (AMP+) and CCL4 was co-expressed with KAS IIIa/KAS IIIb and FatB/FatB2 in BL21(DE3). After IPTG-induction, upon the feeding of 1 g/L of isobutyric acid, 8M was produced (FIG. 7). The SEQ IDS NOs 6 and 7 represent optimized KAS nucleic acid sequences from hot peppers. KAS IIIa (EU616569) and KAS IIIb (EU616570) are genes from hot peppers.

In another example, a PCT gene (NCBI Reference Sequence: WP_014015705.1) from *Megasphaera elsdenii* was synthesized with codon optimization against *E. coli* genome. PCT encodes an acetate CoA-transferase which converts isobutyric acid and acetyl-CoA into isobutyryl-CoA and acetate (McMahon and Prather, 2014). PCT was cloned into pETDuet-1 vector (AMP+) and PCT was co-expressed with KAS IIIa/KAS IIIb and FatB/FatB2 in BL21(DE3). After IPTG-induction, upon the feeding of 1 g/L of isobutyric acid, 8M was produced.

In another example, based on the work of Jiang et al. (2015), alsS and bkd genes from the genome of Bacillus subtilis 168 were cloned into pETDuet-1 vector together with KAS IIIa/KAS IIIb pRSFDuet-1vector respectively, and ilvC and ilvD genes from the genome of E. coli were cloned into the two multiple cloning sites of pACYCDuet-1 vector (CM+), respectively (FIG. 8). When alsS, ilvC, ilvD, bkd and KAS IIIa/KAS Mb genes were co-expressed with FatB/FatB2 in BL21(DE3), after IPTG-induction, 8M was produced from a de novo pathway.

Expression

As described above, to produce 8M, applicants first used three methods to make isobutyryl-CoA namely, de novo, ACS (AAE) or PCT pathways. Then isobutyryl-CoA was used by KAS Ma or KAS IIIb for entering fatty acid elongation cycles of microbial host e.g. E. coli. After three rounds of elongation, 8M was released by FatB or FatB2. pRSFDuet-1 was used to express KAS Ma or KAS Mb; pCDFDuet-1 was used to express FatB or FatB2; pETDuet-1 was used to express ACS (AAE) or PCT; pACYCDuet was used to express ilvC and ilvD; pETDuet to express bkd; pRSFDuet-1 to express alsS and KAS Ma. (See SEQ IDS Nos 1 through 9). The transformed culture in BL21star (DE3) was induced by IPTG. In the case of ACS or PCT pathway were exploited for 8M production, 1 g/L of isobutyric acid was fed into the culture. Fatty acids were extracted with ethyl acetate and methylated with 2.5% sulfuric acid in methanol. Methyl esters of fatty acids were extracted with hexanes and analyzed by GC/MS.

Product Analysis

GC/MS was used to analyze fatty acid composition after the methylation. GC/MS analysis was conducted on Shimadzu GC-2010 system, which with GCMS-QP2010S detector analytical column is: SHRXI-5MS (Thickness 0.25 um; length 30 m; diameter 0.25 mm), injection temperature 265° C. Injection mode was split, furnace temperature 50° C., the temperature gradient: 0-4 min 50° C.; 4-7.3 min 50° C.-100° C., a gradient of 15; 7.3-15.3 min, 100° C.-260° C., a gradient of 20. The identity and presence of the 8M compound in the fermentation product was confirmed by comparing its retention time and mass spectrum with those of an 8M standard purchased from Cayman Chemical (Ann Arbor, Mich.). They were identical.

Production of 8-Methyl Nonanoic Acid

As shown in FIG. 5, the culture system had a titer of ca. 1 mg/L. To produce 8M, cultures from glycerol stock of the E. coli BL21(DE3) strain overexpressing ACS or PCT, KASIIIa or KASIIIb, and FatB or FatB2 were streaked on LB (AMP+Kan+Spect+) plates and incubated at 37° C. overnight. Single colonies were picked to inoculate 5 ml of LB (AMP+Kan+Spect+) liquid medium and the cultures were shaken at 250 rpm at 37° C. overnight. 20 ml of LB (AMP+Kan+Spect+) liquid medium were inoculated with 2% of overnight culture and the culture were shaken at 250 rpm at 37° C. until OD600 reached 0.6 (usually 3 hours). Then the cultures were cooled down to 30° C. and 1 mM IPTG was added to induce protein expression. Three hours later, 1 g/L of isobutyric acid was added and samples were taken for 8M analysis.

To analyze 8M production, 0.5 ml culture was extracted with 0.5 ml ethyl acetate with shaking for 30 minutes. After centrifugation at 14,000 rpm for 10 min, 100 µl of ethyl acetate phase were transfer to a glass tube and dried over nitrogen gas. 1 ml of 2.5% sulfuric acid in methanol and the tube was incubated in a 65° C. water bath for 60 min. Then 2 ml of 0.9% NaCl and 2 ml of hexanes were added to extract methyl esters of fatty acids. After centrifugation at 2500 rpm for 10 min, the hexane phase was injected into GC/MS for the analysis of 8M concentrations as described above.

STATEMENT OF INDUSTRIAL APPLICABILITY/TECHNICAL FIELD

This disclosure has applicability in the food, medicinal, and pharmacological industries. This disclosure relates generally to a method for the biosynthetic production of 8-methyl nonanoic acid via a modified microbial strain.

Sequences of Interest

| Nucleic Acid & Amino Acid Sequences of FAT2B | |
|---|---|
| SEQ ID NO: 1 Fat2B- Nucleic Acid | Atgtcgttgatgatcagggatttgagcagtttacattacacagataatttctggaaaacagagaagcatgtgatggaa tgccggagtttgaaatttgattgtaacgcgaagaagaaatggagagcgataactgctagtgcagacagtagcggaa gcagaagcattgatacaattaatgggaagaagataaatggtgttcatgttgaggggcactcgcaatcaggacaaag gggaaatgtagttgaatcaggatcatcatcatcaccgaaacattcatatatgttagggaattttgtggaggataaggtt gtgtataggcagtcatttgtgattaggtcttatgaaattggacctgataaaactgctactatggaaactatcatgaatctc cttcaggagacagctctaaatcatgtggcgaactcaggggttggtagtagtggattcggggctacacgagagatga gccttaggaaactcatatgggtagtcactcgcatacatatacaaattgaacaatatagctcttggggagatgtggtag agatcgatacatgggtagatgcagcaggcaaaatggaatgagaagggattggatcattcgcgactccaactactc gcaaaatcatcactagagcaacaagtaaatgggtgataatgaacatagaaacaagaaggttatccaaaatcccaga gcaggtcaaagcagaagttcgacctttctacatcaacagattcgcgatccctactgcacaaattgactctgaaaagat tgagaaactcaacgatgaaactgcccaaatcatctcttccgcttagctccgcgatggagcgacatggatgctaatc aacatgtcaacaatgtcaaatatattggatggattttggagagtgtgcccataaatgttttagaagactactacttaatg agcttgacattagagtatagacgtgaatgtcaattatcaaatgtgctgcaatccatgacaactatgcgagaaatagca acatcagcaagtgataaaaattgtggacttgaatgcacacatctgattcgaatggaggctgatcgagctgaggttgtt cgagcaaggtccctatggcagccaaaacagtga<br>-Nucleotide sequence of FatB2, NCBI Reference Sequence: XM_016708605.1 |
| SEQ ID NO: 2 Fat2B- Amino Acid | MSLMIRDLSSLHYTDNFWKTEKHVMECRSLKFDCNAKKKWRAITASAD SSGSRSIDTINGKKINGVHVEGHSQSGQRGNVVESGSSSSPKHSYMLGNF VEDKVVYRQSFVIRSYEIGPDKTATMETIMNLLQETALNHVANSGVGSS GFGATREMSLRKLIWVVTRIHIQIEQYSSWGDVVEIDTWVDAAGKNGM RRDWIIRDSNTRKIITRATSKWVIMNIETRRLSKIPEQVKAEVRPFYINRF AIPTAQIDSEKIEKLNDETAQIISSGLAPRWSDMDANQHVNNVKYIGWIL ESVPINTVLEDYYLMSLTLEYRRECQLSNVLQSMTTMREIATSASDKNCG LECTHLIRMEADRAEVVRARSLWQPKQ<br>-NCBI Reference Sequence: XP_016564091.1 |

Nucleic Acid Sequences of 8M Synthesis Related Thioesterases

SEQ ID NO: 3
FatA-TP

```
Gcgaccaacgaaagagaatctaaaagtaaacagcaggtcagtcacgaaccatcacttgctgatcgtttacgt
ctgggggaccatgagtgaagatggtatgtcatataaagagaaattcatcgttcgctgctatgaagttggcgttaataaa
acgctgacggttgaaacaattgctaatctgctgcaggaagtaggttgtaaccatgcacagagcgtgggcttcagca
cagatggctttgcgactacccatagcatgcgtaaattacatttaatttgggttactgcgcgtatgtatatcgaaatttata
aatatccggcttggtctgatgtcgttgagattgagacatggtgccagagtgaaggacgcatcggtactcgccgcga
ttggatcctgaaagattgtgccacgggggaggtcatcggacgcgccacctcaaaatggctgatgatgaatcagga
tacacgtcgtctgcagaaagttacggatgaggtaagagatgagttagagctgtatttcccgaaagaacttcgcctgg
cttttcctgaagaaaacaatggctcactgaaaaaaaattcctaaattagaagatccggctgaatatagtaaacttggcct
ggtgcctagacgtgcagatctggatatgaatcagcatgtgaacaatgttacatatattggttgggtcttggaaagtatg
ccgcaggagatcatcgatacgcatgagttagggaccattacgattgattatagaagagagtgccagcacgatgatg
ttgtggattctttaacctcagtggaaccgatcgaggatactgatgctttgggtgcaaatgggagcgcgacagcagca
aaagatgttaataaatcagtgctgcattttctgcgtcttagtagtgatggcctggagatcaatagatgtcgcacagagt
ggcgtaaaaaaaccaagccggatttaa
```

SEQ ID NO: 4
FatB-TP

```
GCGAAAGCCAACGCACAGGCTCCGCCGAAAGTGAATGGCACCAAAG
TCGGTGTGATGGATGGCTTTAAAACGGATGACGAAGTTATTAGCTCT
CATCACCCGCGTACCTTCATCAACCAGCTGCCGGATTGGAGCATGCT
GCTGGCGGCCATTACCACGATCTTTCTGGCAGCTGAAAAACAATGGA
TGATGCTGGATTGGAAACCGAAACGTCCGGACATGCTGGTCGATCCG
TTTGGCCTGGGTAAAATTGTGGAAGATGGTTTTATCTTCCGTCAGAA
CTTCTCAATTCGCTCGTATGAAATCGGCGCAGATCGCACCGCTAGTA
TTGAAACGATGATGAACCATCTGCAAGAAACCGCGCTGAATCACGTG
AAATCCGCCGGTCTGATGCATGGCGGTTTCGGCAGTACCCCCGGAAAT
GTCCAAACGTAATCTGATCTGGGTGGTTACGAAAATGCAGGTCGTGC
TGGATCGCTACCCGACCTGGGGTGACGTTGTCCAAGTGGATACGTGG
GTTGCGGCCAGCGGCAAAAACGGTATGCGTCGCGACTGGCTGATTCG
TGATTCTACCACGGGCGACGTTCTGATGCGCGCAAGTTCCCAGTGGG
TCATGATGAATAAAGAAACCCGTCGCCTGAGCAAAATTCCGGATGA
AGCGCGTGCCGAAATCGAAGGTTATTTTGTCGACTCACCGCCGGTGA
TCGATGACGATTCGCGCAAACTGCCGAAACTGGATGAAACCACGGC
AGACTATACCCGCACCGGTCTGACCCCGCGCTGGTCAGACCTGGATG
TGAACCAGCACGTTAACAATGTCAAATACATTGGTTGGATTCTGGAA
TCGGCTCCGATGCAAATTCTGGAAGGCTGCGAACTGGCAGCTATGAC
GCTGGAATACCGTCGCGAATGTCGTCGCGATAGCGTTCTGCAGAGCC
TGACCTCTGTTCTGGATAAAGAAGTCGGCGGTGACCTGACGAACTTT
GGTCATGTGGAATGCCAACACGTTCTGCGCCTGGAAAATGGCGGTGA
AGTGGTTAAAGGCCGTACCGAATGGCGCCCGAAACTGATTAATGGC
ATCGGTTCTCTGGGCGGTTTCCCGGCCTAA
```

SEQ ID NO: 5
FatB2-TP

```
GGTGTCCATGTGGAAGGCCACAGTCAGTCCGGCCAACGCGGTAACGT
GGTTGAATCAGGTAGTTCCTCATCGCCGAAACATTCGTATATGCTGG
GCAATTTTGTGGAAGATAAAGTCGTGTATCGCCAGAGCTTCGTTATC
CGTTCTTACGAAATTGGTCCGGACAAAACCGCGACGATGGAAACCAT
TATGAACCTGCTGCAAGAAACGGCGCTGAACCATGTTGCCAATAGCG
GCGTCGGTAGCTCTGGCTTCGGTGCGACCCGTGAAATGTCACTGCGC
AAACTGATCTGGGTTGTCACGCGTATTCACATCCAGATTGAACAATA
TAGTTCCTGGGGCGATGTGGTTGAAATTGATACCTGGGTGGACGCGG
CCGGCAAAAACGGTATGCGTCGCGATTGGATTATCCGTGACAGCAAT
ACCCGCAAAATTATCACCCGTGCTACGTCTAAATGGGTTATCATGAA
TATTGAAACCCGTCGCCTGAGCAAAATCCCGGAACAGGTGAAAGCC
GAAGTTCGCCCGTTTTACATCAACCGTTTCGCAATTCCGACCGCTCAG
ATCGATAGTGAAAAAATCGAAAAACTGAACGACGAAACGGCGCAAA
TTATCTCATCGGGTCTGGCGCCGCGTTGGTCTGATATGGACGCAAAC
CAGCATGTTAACAACGTCAAATACATCGGCTGGATTCTGAAAGTGT
CCCGATTAATGTGCTGGAAGATTATTACCTGATGTCCCTGACCCTGG
AATACCGTCGCGAATGTCAGCTGAGTAACGTGCTGCAATCCATGACC
ACGATGCGCGAAATCGCGACCTCAGCCTCGGATAAAAATTGCGGCCT
GGAATGTACGCACCTGATTCGTATGGAAGCGGACCGTGCGGAAGTG
GTGCGTGCTCGTTCTCTGTGGCAGCCGAAACAATGA
```

SEQ ID NO: 6
KAS IIIa-TP optimized

```
agtagtaccgttgagggtgcggataaattgagcacggatcagtcacgcgtaagtcgtttggttagtcgcggatgtaa
actgattggctgtggcagtgcggtgccggcattgaaaatctccaacgatgatctggctaaaattgtagatactaatga
tgaatggatcagcgttcgtaccgggatccgtaaccgccgcgtgctgtcaggtaaagataatctgacggatttagctg
cggaagccgcacgcaaagcactggaaatggccgaggtcgatcctaacgatattgatttgattctgctttgttcatcca
cccctgaggatctgtttggcagcgcacctcagattcagaaagctttgggttgcaaaagtaatccactggcgtttgata
ttacagccgcgtgtagcggatttatgctgggtttggtaagcgccgcctgttatattcgcggaggagggttcaaaaac
gtattagtggttggcgcagatgcgctgtcacggtatgtagattggaccgatcgcgggacgtgtattcttttggtgatg
cggcaggggcggttgttatgcaggcctgtgatattggagaggatggtcttttcgggtttgatctgcattctgatggcg
agggtcagcgccatctgaacgcctcctttaaagagaacgagtcagcgtgggcctgcggtaccaacggtagtgttat
tggattcccctccgaaaacgagctcatattcctgtattcagataacggtaaagaagtgttcagatttgctgtgcggt
ggtgcctcagagcatcgggcagcactggagaatgctggcctgcctcagtctaaaattgattggcttctgttacacc
aggcgaatcagcgcatcattgatgcagtcgccacgcgtctggaggtgccgtccgagcatgtgatttctaatttatca
aatattggaaatacatcagcagcgagtattcctctggctctggatgaagcagttcgtagcggtaaagttcaggctgg
gcatgtcattgcagccgctggttttggtgcaggactgacctggggaagcgctattttgagatggggctaa
```

| | |
|---|---|
| SEQ ID NO: 7 KAS IIIb-TP optimized | GCCAAAGGCGCAGTGGAACTGAGCCGTCTGGTTAATACCGGTTGCAA ACTGGTGGGCTGTGGTTCAGCTGTGCCGTCGCTGCGCGTTAGCAACA ATGATCTGGCAAAAATCGTCGATACCAATGACGAATGGATTTCTGTG CGTACGGGCATCCGCCATCGTCGCGTTCTGAGTGGTAAAGAAAACCT GACGGATCTGGCCATCGAAGCGGCCTGGAAAGCTCTGGAAATGGCG GACGTCCCGCCGGAAGATGTGGACCTGATTCTGATGTGCAGCTCTAC CGGCGATGACCTGTTTGGTTCTGCCCCGGTGATCCAGAAAGCACTGG GCTGTAAACGTAATCCGCTGGCGTTCGATATTACGGCAGCTTGCAGT GGCTTTCTGCTGGGTCTGTTCTCAGCTTCGTGTTATATTAAAGCGGGC GGTTTTAAAAACGTCCTGGTGATTGGCGCCGATGCAGTTTCCCGTTTT ATCGATTGGACCGACCGCGGTTCATGCATTCTGTTCGGCGATGCGGC CGGTGCTGTTCTGGTCCAGGCGTGTGATATCGGTGAAGACGGCCTGT TTGGTTTCGATCTGCATTCGGATGGCGACGGTAAACGCCACCTGATT AGCACCTTTAAAGAAAATGAAACGGATGACGCCTCGAACGAAATC ACAGCGTCACCTCTTTCCCGCCGAAATGCAGTTCCTATTCATACCTGC AGATGAACGGCAAAGAAATCTTTAAATTCGCGGTTCGTGTGGTTCCG CAATCCATTGAAGCAGCTCTGGAAAAAGCCGGCCTGGATGGTTCAAA CAATTTTGACTGGCTGCTGCTGCATCAGGCCAACCAACGCATTATCG ATGGCATCGCAACCCGTCTGGAAGTTCCGTCTGAACGCGTCATTAGT AACCTGGCAAATTACGGTAACACGAGTGCCGCATCCATTCCGCTGGC ACTGGATGAAGCAGTGCAGGACGGCAAAGTTCAACCGGGTCACGTC ATTGCAGCGGCCGGTTTTGGTGCCGGTCTGACCTGGGCTAGCGCGAT TTTCCGTTGGGGTTAA |
| SEQ ID NO: 8 CCL4-optimized | ATGGAAGACCTGAAACCGCGTCCGGCATCGTCCTCCCCGCTGACCCC GCTGGGCTTTCTGGAACGTGCTGCGACCGTGTATGGTGACTGCACCT CTGTGGTTTATGATGCGGTTAGCTACACCTGGTCTCAGACGCATCGTC GCTGCCTGTGTCTGGCGAGCTCTATTGCCTCACTGGGCATCGAAAAC GGTCATGTCGTGTCGGTCCTGGCCCCGAATGCCGCAAATGTATGA ACTGCACTTTGCAGTCCCGATGGCAGGTGCTATTCTGAACGCAGTGA ATCTGCGTCTGGATGCTCGCACCATTTCAATCCTGCTGCATCACAGTG AATCCAAACTGATCTTCGTGGATCACCTGTCGCGTGACCTGATTCTG GAAGCGATCGCCCTGTTTCCGAAACAGGCACCGGTGCCGCGCCTGGT TTTCATGGCTGATGAATCAGAATCGGGCAACAGTTCCGAACTGGGTA AAGAATTTTTCTGCTCTTACAAAGATCTGATTGACCGTGGTGATCCG GACTTTAAATGGGTGATGCCGAAAAGCGAATGGGACCCGATGATCCT GAATTACACCTCTGGCACCACGTCATCGCCGAAAGGTGTTGTCCATT GTCACCGCGGCATTTTCATCATGACCGTTGATAGTCTGATTGACTGG GGCGTTCCGAAACAGCCGGTCTATCTGTGGACGCTGCCGATGTTTCA TGCGAATGGTTGGAGCTATCCGTGGGGTATGGCCGCGGTGGGCGGTA CCAATATTTGCCTGCGTAAATTCGATTCTGAAATCATCTACGACATG ATCAAACGCCATGGCGTTACGCACATGTGTGGTGCGCGCGGTGGTTCT GAACATGCTGTCAAATGCCCCGGGTTCGGAACCGCTGAAAACCACG GTGCAAATTATGACCGCAGGTGCACCGCCGCCGAGCGCAGTTCTGTT TCGTACGGGAAAGCCTGGGTTTCGCTGTCTCTCATGGCTACGGTCTGA CCGAAACGGCGGGCCTGGTCGTGAGTTGTGCCTGGAAGAAAGAATG GAACCACCTGCCGGCAACCGAACGTGCTCGCCTGAAATCCCGCCAGG GCGTTGGTACCGTCATGCAAACGAAAATTGATGTTGTCGACCCGGTG ACCGGTGCAGCTGTTAAACGTGACGGCAGTACGCTGGGTGAAGTGGT TCTGCGCGGCCGGTTCCGTGATGCTGGGTTATCTGAAAGATCCGGAAG GCACCGCGAAATCCATGACGGCCGATGGTTGGTTTTATACCGGCGAC GTGGGTGTTATGCATCCGGATGGCTACCTGGAAATCAAAGATCGTAG TAAAGACGTTATCATCTCCGGCGGTGAAAATCTGAGCTCTGTCGAAG TGGAAAGTATTCTGTACTCCCATCCGGACATTCTGGAAGCGCGGGTT GTGGCCCGTCCGGATGAATTTGGGGTGAAACCCGTGCGCCTTCGT GTCACTGAAGAAAGGCCTGACCAAAAAACCGACGGAAAAAGAATT GTGGAATATTGTCGTTCGAAACTGCCGCGCTACATGGTTCCGAAAAC CGTTGTCTTTAAAGAAGAACTGCCGAAAACCAGCACGGGCAAAGTG CAGAAATTCATCCTGCGTGATATGGCTCGTGGTATGGGCTCGGCGAC CGCAGGTGCTTCCCGCTCCCGTATGTAA |
| SEQ ID NO: 9 PCT-optimized | ATGCGTAAAGTGGAAATTATCACCGCGGAACAGGCGGCCCAACTGG TTAAAGATAACGACACCATTACGAGCATCGGTTTTGTCAGCTCTGCA CATCCGGAAGCTCTGACGAAAGCGCTGGAAAAACGTTTCCTGGATAC CAACACGCCGCAGAATCTGACCTATATTTACGCCGGTTCTCAAGGCA AACGTGATGGCCGCGCAGCTGAACATCTGGCTCACACGGGTCTGCTG AAACGCGCGATTATCGGCCACTGGCAGACCGTGCCGGCTATTGGTAA ACTGGCGGTTGAAAACAAAATCGAAGCATACAACTTCAGTCAGGGC ACCCTGGTTCATTGGTTCCGTGCACTGGCTGGTCACAAACTGGGCGT GTTTACGGATATTGGTCTGGAAACCTTCCTGGACCCGCGCCAGCTGG GCGGTAAACTGAACGATGTTACGAAGAAGACCTGGTTAAACTGAT CGAAGTCGATGGCCATGAACAGCTGTTTTATCCGACCTTCCCGGTTA ACGTCGCTTTTCTGCGCGGACACGTACGCGGATGAAAGTGGCAATATT ACCATGGACGAAGAAATCGGTCCGTTCGAATCAACCTCGGTCGCGCA GGCCGTGCATAATTGCGGCGGTAAAGTGGTTGTCCAAGTGAAAGATG TGGTTGCCCACGGTTCCCTGGACCCGCGTATGGTCAAAATTCCGGGC ATCTATGTGGATTACGTCGTGGTTGCGGCCCCGGAAGACCATCAGCA AACGTATGATTGTGAATACGATCCGAGCCTGAGCGGTGAACATCGTG |

```
CACCGGAAGGTGCAACCGATGCAGCTCTGCCGATGTCAGCGAAGAA
AATTATTGGTCGTCGCGGCGCCCTGGAACTGACCGAAAACGCAGTCG
TGAATCTGGGTGTGGGCGCACCGGAATATGTGGCGTCGGTTGCCGGT
GAAGAAGGCATTGCGGATACCATCACGCTGACCGTCGAAGGCGGTG
CCATTGGCGGTGTGCCGCAGGGCGGTGCACGTTTTGGTAGTTCCCGC
AACGCAGATGCTATTATCGACCATACCTATCAGTTTGATTTCTACGAC
GGCGGTGGCCTGGATATTGCCTATCTGGGCCTGGCACAATGCGACGG
TAGTGGCAACATCAATGTTTCCAAATTTGGTACGAATGTCGCCGGCT
GCGGTGGCTTCCCGAACATTTCTCAGCAAACCCCGAATGTTTACTTTT
GTGGCACGTTCACCGCGGGCGGCCTGAAAATTGCGGTGGAAGATGG
TAAAGTTAAAATCCTGCAGGAAGGCAAAGCCAAAAAATTCATCAAA
GCAGTGGATCAAATCACCTTCAACGGTAGCTATGCGGCCCGTAATGG
CAAACATGTTCTGTACATTACGGAACGCTGTGTCTTTGAACTGACCA
AAGAAGGTCTGAAACTGATTGAAGTGGCTCCGGGCATTGATATCGAA
AAAGACATCCTGGCCCACATGGATTTTAAACCGATTATCGACAATCC
GAAACTGATGGATGCGCGTCTGTTCCAGGACGGTCCGATGGGCCTGA
AAAAATAA
```

LITERATURE CITED AND INCORPORATED BY REFERENCE

1. Alum M. et al., *Differential expression of fatty acid synthase genes, Acl, Fat and Kas, in Capsicum fruit.* J Exp Bot.; 54(388):1655-64 (2003).
2. Aza-Gonzalez C. et al., (2011), *Molecular biology of capsaicinoid biosynthesis in chili pepper (Capsicum spp.).* Plant Cell Rep. 30: 695-706.
3. Belza A, Jessen A B. (2005), *Bioactive food stimulants of sympathetic activity: effect on 24-h energy expenditure and fat oxidation.* Eur J Clin Nutr., 59:733-41.
4. Bentley G. J. et al., *Engineering Escherichia coli to produce branched-chain fatty acids in high percentages,* Metab Eng. 38:148-58 (2016).
5. Bosland and Baral, (2007), *'Bhut Jolokia'—The world's hottest known chile pepper is a putative naturally occurring interspecific hybrid,* Hortscience 42:222-24.
6. Batchelor and Jones, (2000), *Determination of the Scoville Heat Value for Hot Sauces and Chilies: An HPLC Experiment,* J. Chem. Educ., 77 (2) p 266.
7. Catchpole et al., (2003), *Extraction of chili, black pepper, and ginger with near critical CO2, propane, and dimethyl ether: analysis of the extracts by quantitative nuclear magnetic resonance,* J. Agricultural and Food Chemistry 51: 4853-60.
8. Caterina MJ., et al., (1997), *The capsaicin receptor: a heat-activated ion channel in the pain pathway,* Nature 389, 816-24.
9. Constant HL et al., (1996), *Nonivamide, a constituent of Capsicum oleoresin,* J. Natural Products, 59: 425-26.
10. Crombie et al., (1955). *Amides of vegetable origin. Part VI. Synthesis of capsaicin,* J. Chem Soc., 1025-27.
11. Curry, J. et al., (1999), *Transcripts for possible capsaicinoid biosynthetic genes are different accumulated in pungent and non-pungent Capsicum spp,* Plant Sci. 148: 47-57.
12. Du J et al., (2011), *Engineering microbial factories for synthesis of value-added products,* J Ind Microbiol Biotechnol. 38: 873-90.
13. Flagan S. F., *Utilization of capsaicin and vanillylamine as growth substrates by Capsicum (hot pepper)-associated bacteria,* Env. Microbiology 8(3) 560-65 (2006).
14. Garces-Claver A. et al., (2007). *Identification, validation and survey of a single nucleotide polymorphism (SNP) associated with pungency in Capsicum spp.* Theor Appl Genet 115: 907-16.
15. Govindarajan and Sathyanarayana (1991), *Capsicum-production, technology, chemistry, and quality. Part V. Impact on physiology, pharmacology, nutrition, and metabolism; structure, pungency, pain, and desensitization sequences,* Critical Reviews in Food Science and Nutrition 29(6):435-74.
16. Haushalter R. W., et al., *Production of anteiso-branched fatty acids in Escherichia coli; next generation biofuels with improved cold flow properties,* Metab. Eng. 26:111-18 (2014).
17. Häusler A, and Munch T., (1997), *Microbial production of natural flavors,* ASM News 63:551-59.
18. Higashiguchi F., et al., (2006) *Purification and structure determination of glucosides of capsaicin and dihydrocapsaicin from various Capsicum fruits,* J Agric Food Chem. 54: 5948-5953.
19. Howard T. P., et al., *Synthesis of customized petroleum-replica fuel molecules by targeted modification of free fatty acid pools in Escherichia coli.* Proc Natl Acad Sci USA 110:7636-41 (2013).
20. Jiang W., et al., *Enhanced production of branched-chain fatty acids by replacing β-ketoacyl-(acyl-carrier-protein) synthase III (FabH),* Biotechnol Bioeng. 112: 1613-22 (2015).
21. Jordt S E. and Julius D., (2002), *Molecular basis for species-specific sensitivity to "hot" chili peppers.* Cell. 108: 421-30.
22. Kaminaga Y. et al., (2004) *Molecular cloning and characterization of a glucosyltransferase catalyzing glucosylation of curcumin in cultured Catharanthus roseus cells.* Febs Lett. 567: 197-202.
23. Kometani, T. et al., (1993) *Glucosylation of capsaicin by cell suspension cultures of Coffea arabica.* Biosci. Biotechnol. Biochem. 57, 2192-2193.
24. Liang Y. T., et al., *Capsaicinoids lower plasma cholesterol and improve endothelial function in hamsters,* Eur J Nutr. 52: 379-88 (2013).
25. Lindsey K. and Yeoman M., *The synthetic potential of immobilised cells of Capsicum frutescens mill cv. annuum.* Planta 162 495-501 (1984).
26. McMahon M. D., and Prather K. L., *Functional screening and in vitro analysis reveal thioesterases with enhanced substrate specificity profiles that improve short-chain fatty acid production in Escherichia coli.* Appl Environ Microbiol. 80: 1042-50 (2014).
27. Mazourek, et al., (2009). *A Dynamic Interface for Capsaicinoid Systems Biology,* Plant Phys., 150:1806-21.
28. Ogawa K., et al., *Evidence of capsaicin synthase activity of the Pun1-encoded protein and its role as a determinant of capsaicinoid accumulation in pepper,* BMC Plant Biol. 15: 93 (2015).

29. Prasad B C., (2006), *Characterization of capsaicin synthase and identification of its gene (csyl) for pungency factor capsaicin in pepper (Capsicum sp.)*. PROC NAIL ACAD SCI USA. 103: 13315-20.
30. Prasad Bc. et al., (2008 *Characterization of capsaicin synthase and identification of its gene (csyl) for pungency factor capsaicin in pepper (Capsicum sp.)*. PROC NATL ACAD SCI USA. 105: 20558.
31. Qin C., et al., *Whole-genome sequencing of cultivated and wild peppers provides insights into Capsicum domestication and specialization*, PROC. NAT'L ACAD. SCI. USA. 111: 5135-40 (2014).
32. Reilly C A. et al., (2001 *Determination of capsaicin, dihydrocapsaicin, and nonivamide in self-defense weapons by liquid chromatography-mass spectrometry and liquid chromatography-tandem mass spectrometry*. J. CHROMATOGR A. 912: 259-67.
33. Stewart C. et al., (2005) *The Pun1 gene for pungency in pepper encodes a putative acyltransferase*, PLANT J. 42: 675-88.
34. Stewart C. et al., (2007) *Genetic control of pungency in C. chinense via the Pun1 locus*. J EXP BOT. 58: 979-91.
35. Shimoda. K., et al., (2007) *Glycosylation of capsaicin and 8-nordihydrocapsaicin by cultured cells of Catharanthus roseus*. PHYTOCHEMISTRY 68: 1391-96.
36. Shockey J M. Et a., (2003), *Arabidopsis contains a large superfamily of acyl-activating enzymes: phylogenetic and biochemical analysis reveals a new class of acyl-coenzyme A synthetases*. PLANT PHYSIOL 132 1065-76.
37. Stewart C., et al., *The Pun1 gene for pungency in pepper encodes a putative acyltransferase*, PLANT J. 42: 675-88 (2005).
38. Suzuki T. et al., (1980) *Intracellular localization of capsaicin and its analogs capsaicinoid in Capsicum fruit, microscopic investigation of the structure of the placenta of Capsicum annuum var annuum cv. Karayatsubusa*. PLANT CELL PHYSIOL 21 839-53.
39. Suzuki T and Iwai K, (1984), *Constituents of red pepper spices: chemistry, biochemistry, pharmacology* and *food science of the pungent principle of Capsicum species*. In A Brossi, ed, THE ALKALOIDS: CHEMISTRY AND PHARMACOLOGY, Vol 23. Academic Press, Orlando, Fla., pp 227-99.
40. Tao H., et al., *Metabolic engineering of microbes for branched-chain biodiesel production with low-temperature property*, BIOTECHNOL BIOFUELS. 8:92 (2015).
41. Thomas B V. Et al., (1998), *Simple method for quantitation of capsaicinoids in peppers using capillary gas chromatography*. J AGRIC FOOD CHEM., 46:2655-63.
42. Tominaga M. and Tominaga T., (2005), *Structure and function of TRPV1*, PFLUGERS ARCH. EUR J PHYSIOL.; 451: 143-50.
43. Xu H., et al., *Characterization of the formation of branched short-chain fatty acid: CoAs for bitter acid biosynthesis in hop glandular trichome*, MOL., PLANT. 6: 1301-17 (2013).
44. Walsh and Hoot, (2001), *Phylogenetic relationships of Capsicum (Solanaceae) using DNA sequences from two noncoding regions: The chloroplast atpB-rbcL spacer region and nuclear waxy introns*, INT. J. PLANT SCI. 162: 1409-18.
45. Weber N. et al., (2014), *Biocatalytic potential of vanillin aminotransferase from Capsicum chinense*. BMC BIOTECHNOL. 14:25.
46. Yao et al., (1994), *Supercritical carbon dioxide extraction of Scotch Bonnet (Capsicum annuum) and quantification of capsaicin and dihydrocapsaicin*, J. AGR. FOOD CHEM. 42:1303-05.

PATENTS CITED AND INCORPORATED BY REFERENCE

1. Chen H. et al., (2015) Methods of using capsaicin synthase for the microbial production of capsaicinoids. PCT/US2015/011729.
2. Chen et al., U.S. Pat. No. 5,094,782.
3. LaHann et al., U.S. Pat. No. 4,493,848.
4. Zhou R., and Yu X., (2014) Methods of making vanillin via the microbial fermentation of ferulic acid from eugenol using a plant dehydrogenase. PCT/US2014/063952.

What is claimed is:

1. A biosynthetic method of producing 8-methyl nonanoic acid (8M) comprising:
   a) expressing a KASIIIa gene, a KASIIIb gene and one or more genes encoding an acyl-acyl carrier protein (ACP) thioesterase in a transformed cellular system;
   b) feeding or producing isobutyryl-CoA in said transformed cellular system; and,
   c) producing 8-methyl nonanoic acid;
   wherein the KASIIIa gene comprises a nucleic acid sequence that is at least 90% identical to SEQ ID NO. 6 and the KASIIIb gene comprises a nucleic acid sequence that is at least 90% identical to SEQ ID NO. 7.

2. The biosynthetic method of claim 1, wherein the one or more genes encoding an acyl-(ACP) thioesterase comprise at least one fatty acyl-ACP thioesterase B is (FATB) gene cloned from a plant of the *Capsicum* genus.

3. The biosynthetic method of claim 2, wherein the one or more genes encoding an acyl-(ACP) thioesterase comprise a fatty acyl-ACP thioesterase B (FATB2) gene, said FATB2 gene comprising a nucleic acid sequence that is at least 90% identical to SEQ ID NO. 5.

4. The biosynthetic method of claim 3, wherein the one or more genes encoding an acyl-(ACP) thioesterase further comprise a fatty acyl-ACP thioesterase B gene comprising a nucleic acid sequence that is at least 90% identical to SEQ ID NO. 4.

5. The biosynthetic method of claim 1, wherein said transformed cellular system is selected from the group including yeast, non-capsaicinoid producing plants, algae and bacteria.

6. The biosynthetic method of claim 5, wherein said cellular system is *E. Coli*.

7. The biosynthetic method of claim 1, further comprising purifying said 8M to at least 70% purity.

8. The biosynthetic method of claim 1, wherein isobutyryl-CoA is produced in said transformed cellular system by feeding isobutyric acid and co-expressing an acyl-CoA synthetase (ACS) gene in said transformed cellular system.

9. The biosynthetic method of claim 8, wherein said ACS gene encodes an isobutyryl-CoA synthetase which converts isobutyric acid into isobutyryl-CoA.

10. The biosynthetic method of claim 8, wherein ACS gene is CCL4 gene comprising a nucleic acid sequence that is at least 90% identical to SEQ ID NO. 8.

11. The biosynthetic method of claim 1, wherein isobutyryl-CoA is produced in said transformed cellular system by feeding isobutyric acid with acetyl-CoA and co-expressing a propionate-CoA transferase (PCT) gene in said transformed cellular system.

12. The biosynthetic method of claim 11, wherein said PCT gene encodes a propionate-CoA transferase that converts isobutyric acid and acetyl-CoA into isobutyryl-CoA and acetate.

13. The biosynthetic method of claim 12, wherein said acetate-CoA transferase gene is a PCT gene comprising a nucleic acid sequence that is at least 90% identical to SEQ ID NO. 9.

14. The biosynthetic method of claim 1, wherein isobutyryl-CoA is produced in said transformed cellular system by feeding glucose and co-expressing alsS, ilvC, ilvD and bkd genes in said transformed cellular system.

15. The biosynthetic method of claim 14, wherein the alsS and bkd genes are cloned from *Bacillus subtilis*.

16. The biosynthetic method of claim 14, wherein the ilvC and ilvD genes are clone from *E. coli*.

* * * * *